(12) United States Patent
Wandell et al.

(10) Patent No.: US 7,569,184 B2
(45) Date of Patent: Aug. 4, 2009

(54) QUANTITATIVE ANALYSIS OF A BIOLOGICAL SAMPLE OF UNKNOWN QUANTITY

(75) Inventors: Michael Wandell, Mercer Island, WA (US); Ilia Vinogradov, Elmhurst, IL (US); Barbara Godsey, Long Grove, IL (US); Troy Bervig, Chicago, IL (US)

(73) Assignee: Home Access Health Corporation, Hoffman Estates, IL (US)

( * ) Notice: Subject to any disclaimer, the term of this patent is extended or adjusted under 35 U.S.C. 154(b) by 800 days.

(21) Appl. No.: 10/982,199

(22) Filed: Nov. 5, 2004

(65) Prior Publication Data

US 2005/0209532 A1    Sep. 22, 2005

Related U.S. Application Data

(63) Continuation-in-part of application No. 10/706,321, filed on Nov. 12, 2003, which is a continuation-in-part of application No. 10/421,086, filed on Apr. 23, 2003.

(60) Provisional application No. 60/374,629, filed on Apr. 23, 2002.

(51) Int. Cl.
 *B01L 3/00*      (2006.01)
 *G01N 33/92*    (2006.01)
 *G01N 31/00*    (2006.01)
 *G01N 33/72*    (2006.01)

(52) U.S. Cl. .............................. 422/61; 436/71; 436/16; 436/17; 436/19; 436/66

(58) Field of Classification Search .................. 422/61; 436/71, 16, 17, 19, 66
 See application file for complete search history.

(56) References Cited

U.S. PATENT DOCUMENTS 4,839,296 A    6/1989    Kennedy et al.

(Continued)

FOREIGN PATENT DOCUMENTS

EP    0 419 196 A2    3/1991

(Continued)

OTHER PUBLICATIONS

Felix Wroblewski and John S. Ladue; Serum Glutamic Pyruvie Transaminase in Cardiac and Hepatic Disease; Proceedings of the Society for Experimental Biology and Medicine; Jan.-Apr. 1956, vol. 91, New York.

(Continued)

*Primary Examiner*—Jill Warden
*Assistant Examiner*—Lore Ramillano
(74) *Attorney, Agent, or Firm*—Vedder Price P.C.

(57) ABSTRACT

Disclosed is a method for testing a modified specimen such as a dried blood spot, plasma or serum specimen, for an analyte of interest, such as cholesterol. In accordance with the disclosed subject matter, the level of the analyte of interest in the medium from which the modified specimen was obtained (e.g., from a patient's blood) is determined based on the level of an analyte in a solution formed from the modified specimen and on the level of at least one normalizing analyte. The analyte and normalizing analyte each may be an ion, compound, biochemical entity, or property of the specimen. Also disclosed are a fluid collector and a fluid collection device.

12 Claims, 12 Drawing Sheets

U.S. PATENT DOCUMENTS

| | | | |
|---|---|---|---|
| 5,001,067 A * | 3/1991 | Coleman et al. | 436/63 |
| 5,435,970 A | 7/1995 | Mamenta et al. | |
| 5,935,775 A | 8/1999 | Savjani | |
| 5,978,466 A | 11/1999 | Quattrocchi | |
| 6,008,059 A | 12/1999 | Schrier et al. | |
| 6,014,438 A | 1/2000 | Quattrocchi | |
| 6,016,345 A | 1/2000 | Quattrocchi | |
| 6,036,659 A * | 3/2000 | Ray et al. | 600/573 |
| 6,040,135 A | 3/2000 | Tyrrell | |
| 6,066,448 A | 5/2000 | Wohlstadter et al. | |
| 6,066,464 A | 5/2000 | Khosravi et al. | |
| 6,187,531 B1 | 2/2001 | Tyrrell | |
| 6,226,378 B1 | 5/2001 | Quattrocchi | |
| 6,730,501 B2 * | 5/2004 | Eyre et al. | 435/91.2 |
| 2001/0055784 A1 | 12/2001 | Noda et al. | |
| 2002/0026331 A1 * | 2/2002 | Case | 705/3 |
| 2002/0055176 A1 | 5/2002 | Ray | |

FOREIGN PATENT DOCUMENTS

| | | |
|---|---|---|
| EP | 0 503 356 B1 | 10/1996 |
| WO | WO 00/44930 | 8/2000 |
| WO | WO 03/091736 | 11/2003 |

OTHER PUBLICATIONS

Michael McGowan, Joseph D. Artiss, Donald R. Strandbergh, and Bennie Zak; A peroxidase-Coupled Method for the Colorimetic Determination of Serum Triglycerides; Journal of the American Association for Clinical Chemistry; vol. 29, No. 1, Jan. 1983.

Charles C. Allain, Lucy S. Poon, Cicely S.G. Chan, W. Richmond, and Paul C. Fu; Enzymatic Determination of Total Serum Cholesterol; Clinical Chemistry, vol. 20, No. 4, 1974.

Callum G. Fraser, Steven T. Cummings, Stephen P. Wilkinson, Ronald G. Neville, James D. E. Knox, Olga Ho, and Ronald S. MacWalter; Biological Variability of 26 Clinical Chemistry Analytes in Elderly People; Clinical Chemistry, vol. 35, No. 5, 1989.

M.D. Penney and G. Walters; Are osmolality measurements clinically useful?; Journals of Clinical Biochemistry; vol. 24, Part 6, Nov. 1987.

Bradley P. Carlin and Thomas A. Louis; Bayes and Empirical Bayes Methods for Data Analysis; Texts in Statistical Science, 2000, pp. 17-46, Second Edition.

Nader Rifai and G. Russell Warnick; Laboratory Measurement of Lipids, Lipoproteins and Apolipoproteins; American Association of Clinical Chemistry, 1994, pp. 65-107.

Ravel, Richard; Clinical Laboratory Medicine; Sixth Edition, 1995, pp. 171-172, 405-413 and 417-420.

Erhardt, Juergen G et al.; Combined measurement of retinol and soluble transferring receptor (sTfR) in a single dired blood spot (DBS) stored at room temperature; Faseb Journal; vol. 16, No. 4, Mar. 20, 2002, pp. A247-A248, XP009019440; Annual Meeting of the Professional Research Scientists on Experimental Biology; New Orleans, Louisiana, USA; Apr. 20-24, 2002.

Erhardt, Juergen G et al.; Rapid and Simple Measurement of Retinol in Human Dried Whole Blood Spots; Journal of Nutrition; vol. 132, No. 2, Feb. 2002; pp. 318-321, XP002258787.

O'Brien J M et al.; Detection of Hepatitis C Antibody with At-Home Collection Kits Using an Innovative Laboratory Algorithm; Infectious Diseases in Clinical Practice; 2001 USA; vol. 10, No. 9, pp. 474-480; XP00115589.

Erhardt J G et al, "Rapid and simple measurement of retinol in human dried whole blood spots", Journal of Nutrition. Wistar Institute of Anatomy and Biology, Feb. 2002, pp. 318-321, vol. 132, No. 2, Philadelphia, PA, USA [XP-002258787].

Palardy J et al., "Blood Glucose Measurements During Symptomatic Episodes in Patients With Suspected Postprandial Hypoglycemia", New England Journal of Medicine, Nov. 23, 1989, pp. 1421-1425, vol. 321, No. 21, Massachusetts Medial Society, USA [XP009061174].

Howe, Christopher J et al., "Use of filter paper for sample collection and transport in steroid pharmacology", Clinical Chemistry, 1997, pp. 1408-1415, vol. 43, No. 8 Part 1. [XP-002366288].

International Search Report for PCT/US2005/040051.

Written Opinion for PCT/US2005/040051.

* cited by examiner

QUANTITATIVE ANALYSIS OF A BIOLOGICAL SAMPLE OF UNKNOWN QUANTITY

RELATED APPLICATIONS

This application is a continuation-in-part of U.S. patent application Ser. No. 10/706,321, filed Nov. 12, 2003, which was a continuation-in-part of U.S. patent application Ser. No. 10/421,086, filed Apr. 23, 2003, which claims priority to prior Application No. 60/374,629 filed Apr. 23, 2002. All prior applications are hereby incorporated by reference in their entireties.

TECHNICAL FIELD OF THE INVENTION

The invention is in the field of testing, in particular quantitative testing, and in preferred embodiments medical testing. In highly preferred embodiments, the invention is directed towards the testing of body fluid specimens, in particular blood or serum specimens.

BACKGROUND OF THE INVENTION

Modern medical and wellness practices increasingly make use of self-administered tests and self-collection of test specimens. For instance, U.S. Pat. Nos. 5,978,466; 6,014,438; 6,016,345; and 6,226,378, issued to Richard Quattrocchi and assigned to Home Access Health Corporation of Hoffman Estates, Ill., all disclose a method of anonymously testing for a human malady. In accordance with certain embodiments of the subject matter disclosed in the foregoing patents, a patient obtains a blood specimen, typically by pricking his or her finger, and allows the blood to wick onto a blood spot card. After the card has dried, the user then sends the blood spot card to a medical testing facility, where it is tested to determine whether the patient is afflicted with a specific malady. The user may contact the facility anonymously to receive the test result.

The subject matter of the foregoing patents is usable in connection with testing for the presence of human antibodies directed against viral antigens in the blood, for instance, in determining whether a patient is infected with HIV (human immuno-deficiency virus) or with a hepatitis virus. Another document, U.S. Pat. No. 5,435,970, issued to Mamenta et al. and assigned to Environmental Diagnostics, Inc. of Burlington, N.C., discloses a device for separating blood cells from biological fluids, for instance, for separating serum from whole blood. The device disclosed in the '970 patent purports to enable the shipment and testing of a serum sample.

The blood spot and serum specimen cards known in the art are suitable for use in the collection of specimens for qualitative testing, i.e., testing for the presence or absence of a given compound in blood or a given medical condition. Heretofore, however, such blood spot and serum cards have been somewhat unsatisfactory in the quantitative testing of blood and serum specimens.

For instance, general wellness protocol indicates the measurements of a patient's total cholesterol value, which is the number of milligrams of total cholesterol in a deciliter of blood. The value is often used in conjunction with a full lipid profile, which provides levels of triglycerides, HDL (high density lipoprotein) cholesterol, and LDL (low density lipoprotein) cholesterol in a patient's blood. It can be very difficult to gauge the amount of blood or serum that is present in the blood or serum spot card. Particularly when the blood or serum spot card has been self-prepared by a person without medical training, it is difficult to know to certainty whether the spot card has been "underfilled" with less than the intended quantity of blood or serum or "overfilled" with more than the intended quantity. If the amount of blood and serum varies by even a small amount over or under the expected level, the usefulness of the quantitative test can be severely diminished. For instance, it is generally thought that a person's total cholesterol number should be under 200 mg/dl, with cholesterol numbers above 240 mg/dl being considered high and with intermediate cholesterol number being deemed borderline. A 10% margin of error in a cholesterol determination of 220 mg/dl provides no information as to whether the person's cholesterol level is low, intermediate, or high.

In recognition of these problems, the prior art has provided attempts to provide a quantitative determination of analyte levels in a blood specimen. For instance, U.S. Pat. No. 6,040,135, issued to Steven Tyrell and assigned to Biosafe Laboratories, Inc., Chicago, Ill., purports to disclose a method for correcting for blood volume in a serum analyte determination. The method that is purportedly disclosed by this document is limited and is believed generally to be somewhat unsatisfactory.

The invention seeks to improve upon prior art testing methods, and to provide a method for quantitative testing of modified specimens such as dried blood spot and dried serum specimens.

THE INVENTION

The invention provides multiple embodiments in the field of testing, in particular medical testing. In accordance with the invention, a modified specimen, preferably a dried blood fluid sample, such as a dried serum or dried whole blood specimen of unknown quantity, is eluted (re-solubilized) and then tested for an analyte. The level of analyte in the blood from which the modified blood specimen was obtained is determined from the level of analyte in a solution formed from the blood specimen. A normalizing analyte, which in the preferred embodiment is sodium ion, chloride ion, and/or osmolality, is measured and is used in conjunction with the solution level of analyte to determine the level of analyte in the blood from which the modified specimen was obtained. The invention is not limited to the field of medical testing but, to the contrary, is useful in connection with other forms of testing. The invention further provides methods for preparing a database of test results, for preparing a regression using a database of test results, and for providing test results to a user.

In alternative embodiments the invention further encompasses a fluid collector that includes an absorbent substrate coated with a saccharide. A device that includes the collector (as described hereinbelow) also is encompassed by these embodiments.

Other features of preferred embodiments of the invention are set forth hereinbelow.

DESCRIPTION OF THE PREFERRED EMBODIMENTS

Figure 1:
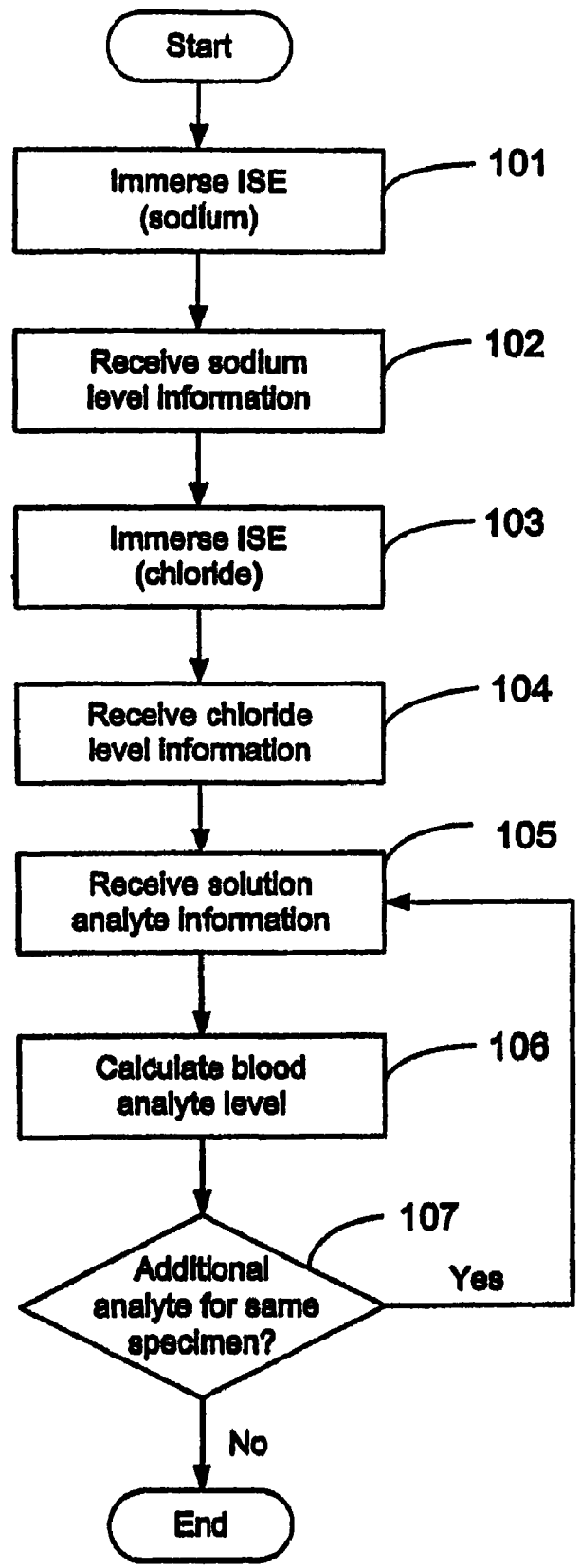
FIG. 1 is a flowchart representing steps in a method for calculating the level of an analyte in blood from which a blood specimen was obtained.

The invention is applicable to the testing of any specimen that is modified from its original form prior to testing. Most commonly, the specimen is a dried specimen, which has been dried to facilitate storage or transport of the specimen or for other purposes. In preferred embodiments of the invention, the specimen is a medical specimen, and in highly preferred embodiments of the invention, the specimen is a blood fluid specimen, by which is contemplated a dried blood spot, a dried serum spot (for instance, as obtained from the device disclosed in U.S. Pat. No. 5,435,970 or that shown in U.S. Pat. No. 4,839,296 issued to Kennedy, et al. and assigned to Chem-Elec, Inc. of North Webster, Ind.), or another blood fluid specimen. The invention is applicable to the testing of the modified specimen for any suitable purpose, and in particular to testing for any analyte in the specimen. For instance, when the specimen is a blood fluid specimen, the test may be a test for prostate specific antigen (PSA), alanineamino transferase (ALT), lipids, such as triglycerides, high density lipoprotein (HDL), low density lipoprotein (LDL), or any other analyte of interest. The invention is applicable to the determination of the level of analyte in the original specimen, for instance, the level of total cholesterol in the blood from which a blood fluid specimen has been obtained. The "level" of the analyte can be expressed in any suitable units, such as molar concentration, weight concentration, or the like. Blood serum is particularly preferred, but it is contemplated that other fractions such as cells, platelets, gamma globulins, plasma or the like may be employed. For instance, it may be designed to test blood cells in connection with a fasting plasma glucose test. More generally, any body fluid is susceptible to analysis in conjunction with the invention. In light of the foregoing, the preferred embodiments of the invention will be further described with respect to the determination of the lipid profile in a blood sample, but it should be understood that the invention is not limited thereto.

The facility or other entity that performs the test of the blood fluid specimen may or may not be the same entity that calculates the level of the analyte in the blood fluid specimen or the entity that receives an inquiry from a user and reports the test results to the user. To test the blood fluid specimen, the specimen is first received by the testing entity and is eluted with a liquid, preferably deionized water. It is contemplated that the liquid may be a non-aqueous liquid or may be an aqueous solution, preferably a solution that is free or essentially free of sodium ions or any other normalizing analyte. Alternatively, the solution may have a known amount of the normalizing analyte that can be taken into account during normalization. Preferably, when the testing entity is a testing facility that is intended to test numerous specimens, the eluant is added in a standard amount, which typically is 600 μl (0.6 ml). The eluant in some embodiments may be a buffered electrolyte solution.

After eluting the specimen, preferably the specimen first is tested for the content of a normalizing analyte, such as sodium and chloride content, and in some embodiments osmolality, which generally represents total content of sodium, glucose, and blood urea nitrogen (BUN). To test for sodium and chloride, an ion specific electrode (ISE), such as that sold by Orion may be employed. Preferably, information concerning both the sodium and the chloride content of the solution are obtained, the information being, for instance, analog information such as an electrical signal or digital information such as a printout representing the sodium or chloride content or a digital signal containing information concerning the sodium or chloride content. Most preferably, osmolality also is measured. It should be noted that the invention is not limited to the use of sodium or chloride as normalizing analytes, but to the contrary, any other analyte (which includes a property such as osmolality) may be measured. It is contemplated in preferred embodiments that the sodium, chloride, and osmolality levels are measured against a predetermined range to determine whether the amount of serum is sufficient to perform an adequate test. For instance, it is contemplated that for a cholesterol test, there ideally should be at least approximately 15-17 μl of serum available for testing. If the sodium content of the eluted solution demonstrates that the serum level is far outside this range, the specimen may be rejected as unsuitable for testing. Generally, the specimen may be rejected if there is insufficient serum in the solution, although it is contemplated that in some cases excess serum may be grounds for rejection. Persons skilled in the art may determine how far outside of the desired range the content of normalizing analyte may be allowed to vary without triggering rejection of the specimen.

Before or after the levels of the normalizing analytes are determined (but preferably after), the solution can be split into four aliquots, or "channels." Each channel is then respectively tested for triglyceride level, HDL level, LDL level, and in a preferred embodiment, ALT level (which may be of interest in informing a physician whether the patient has an abnormal liver which would contraindicate the use of certain drugs). The analyte levels are measured using any technique known in the art or otherwise found to be suitable. For instance, a cholesterol test is disclosed in Allain, C. C., Poon, L. S., Chan, G. S. G., Richmond, W., and Fu, P. C., *Clin. Chem.* 20:474-75 (1974); see also Roeschlau, P. Brent, E. and Gruber, W A., *Clin. Chem. Clin. Biochem.* 12:226 (1974). A test for HDL is disclosed in RiFai, N., Warnick, G. R., Ed., *Laboratory Measurement of Lipids, Lipoproteins, and Apo-*

*lioproteins* (1994). A test for triglycerides is disclosed in McGowan, M. W., Artiss, J. D., Strandbergh, D. R., Zak, B. *Clin. Chem.* 29:583 (1983). A test for the liver enzyme ALT is disclosed in Wroblewski, F., LaDue, J. S., *Proc. Sec. Exp. Biol. Med.* 34:381 (1956). The invention is not limited to the foregoing tests or analytes, but to the contrary is applicable to other tests for these or other analytes.

After the analyte levels have been measured, the level of at least one analyte (and preferably all analytes) in the blood from which the blood fluid specimen was obtained is calculated or otherwise determined based on the solution level of the analyte and on the solution level of at least one normalizing analyte. It is contemplated that the calculation of a blood analyte level may be as simple as multiplying the solution analyte level by the ratio of the blood normalizing analyte level to the solution normalizing analyte level, the blood normalizing analyte level being estimated based on the mean of a normal population distribution. For instance, it is believed that the normal blood sodium level in humans ranges from 136 to 142 mEq/L with a mean of 139 mEq/L and the normal chloride level ranges from 95 to 103 mEq/L with a mean of 99 mEq/L. It is contemplated that through the use of two normalizing analytes, the blood analyte level may be determined by calculating the blood analyte level based on the first normalizing analyte level, calculating the blood analyte level based on the second normalizing analyte level, and then calculating the mean average of the blood analyte levels thus determined.

If additional normalizing analytes are evaluated, the mean average of all blood level analytes thus determined may be calculated; if desired, where there are at least two normalizing analytes, the average may be weighted towards a specific normalizing analyte. For instance, it is contemplated that Bayesian statistical methods may be used to assign a relative weight to the blood analyte levels determined with reference to each analyte. Such statistical techniques may take into account not only the absolute magnitude of the level of the normalizing analyte level but also the difference between the actual level and the magnitude expected based on the expected amount of serum, and the standard deviation of the normal population distribution of the analyte. These techniques, sometimes referred to as "maximum likelihood" or "prior probability analysis" techniques, may be used to provide an approximation of the blood analyte level. Further testing concerning such statistical techniques may be found in Casella, G., Berger, R. L., *Statistical Inference* (1990) and Carlin, B. P., Louis, T. A., *Bayes and Empirical Bayes Methods for Data Analysis* (2d Ed. 2000).

Further details concerning the distribution of sodium, chloride, and osmolality in the normal human population may be found in Ravel, *Clinical Laboratory Medicine* (6th Ed. 1995); see also Penney, M. D. and Walters, G., *Ann. Clin. Biochem.* 24:566-71 (1987) and Fraser, C. G., Cummings, S. T. Wilkinsen, S. O. et al., *Clin Chem.* 35:783-86 (1985). It is further contemplated that a more complicated function of solution analyte level and the levels of one or more normalizing analytes may be employed to calculate the blood analyte levels.

With reference now to FIG. 1, the generalized method shown therein is applicable where the same entity performs the test and calculates the blood analyte level. Thus in steps 101 and 102 respectively the ISE (e.g., sodium) is immersed into the solution, and sodium level information is obtained. The steps are repeated for the receipt of chloride information, as shown in steps 103 and 104. Information concerning the analyte of interest is received in step 105, and the blood analyte level is calculated in step 106. If, in step 107, it is desired to test an additional analyte for the same specimen, control passes to step 105 where the solution analyte information is received for the new analyte. It is contemplated that the steps of testing for the analytes of interest and the normalizing analytes may be performed by one entity and that the calculation of the blood analyte level may be performed by a separate entity. Thus, for instance, in FIG. 1, steps 101 and 103 may be omitted if the entity calculating the blood analyte level is not the same entity as the entity that performs the test. The method outlined in FIG. 1 is very general, and other steps may be added, steps may be omitted or performed in a different order, and more generally the method may be otherwise performed. For instance, steps of elution and verifying proper serum level are not shown, but are preferably employed.

In calculating the analyte level, it has been discovered that it is often desirable to add or subtract a "recovery delta" from the amount of analyte measured in solution, and to base the calculation of one analyte relative to normalizing analyte or analytes on the recovery delta corrected solution analyte level. While it is not wished to be bound by any particular theory of operation, it is believed that, in some instances, analyte will be lost on the strip. As a general matter, the total loss of analyte will be proportional to the amount of analyte originally present on the strip. In some instances, however, as the amount of analyte increases, the proportional analyte loss is believed to decrease. The analyte is thought to "saturate" potential binding sites on the strip. The addition or subtraction of the recovery delta is intended to correct for this phenomenon.

In other cases, particularly in the measurement of HDL, certain analytes can give a "false positive" for which correction is desired. In the Wako HDL assay, HDL is detected after the LDL (and VLDL) molecules are protected from enzymes by certain antibodies. The remaining lipoproteins, which are attacked by enzymes and analyzed, normally are deemed to consist of solely HDL. This assumption generally holds true for venous blood samples. However, elution from a blood collection device in accordance with the invention sometimes yields partially denatured LDL and VLDL molecules. These molecules cannot be protected by antibodies and accordingly are susceptible to enzymatic attack in the same fashion as is HDL, thus providing a false measurement of HDL. The recovery delta thus is of the opposite sign than the recovery delta heretofore described.

In light of the foregoing, it should be appreciated that the recovery delta may be a positive value or a negative value. In accordance with some embodiments of the invention, the inventive method is deemed to encompass the determination of a recovery delta for a particular analyte and set of testing conditions. The recovery delta may be estimated or may be determined empirically, with reference to the data taken from known samples.

Another potential corrective factor takes into consideration the decay of the analyte, which is generally based on time since the sample has been taken from a patient, and which sometimes depends on climactic or other environmental factors. In subtracting or adding a recovery delta to the measured solution analyte level, the recovery delta may be determined according to the following formula:

$$A+B \text{ (time)}$$

wherein A is a positive, zero, or negative value and wherein B is a positive or negative value. Values A and/or B may be determined or estimated based on climactic conditions, to account for different decay rates. Alternatively, the recovery delta may be calculated as a function of time and/or climactic conditions such as humidity, temperature, or the like in a multivariate manner that may be first order or not first order with respect to any of such variables.

The preferred normalizing analytes are sodium and chloride. It has been discovered that the calculation of blood analyte levels based on sodium and on chloride each may be made by assuming a linear relationship between normalizing analyte levels and blood analyte levels. In other words, for sodium, the blood analyte level may be determined in accordance with the following generalized equation:

$$BAL=(\text{solution analyte level}-\text{recovery delta})(A+BX)$$

wherein BAL is calculated blood analyte level, X is the normalizing analyte level, and A and B are calculated or empirically determined or otherwise predetermined constants. Surprisingly, however, it has further been found that the resulting analyte calibration curve often is not linear. For instance, with respect to chloride, the calibration of the ion specific electrode frequently underestimates chloride levels at concentrations lower than 138 mEq/L, and frequently overestimates chloride levels higher than 138 mEq/L. Accordingly, in accordance with highly preferred embodiments of the invention, calculation of analyte level in the blood from which the blood fluid specimen was taken includes a predetermined nonlinear chloride correction factor. In the embodiment of the invention, a nonlinear connection function may be used for chloride but not for sodium.

It is contemplated that the analyte level, first normalizing analyte level, and second normalizing analyte level may be independently determined and these values used to calculate the blood level of the analyte. For instance, the cholesterol tests hereinbefore discussed typically are performed via enzymatic techniques in which the optical density of a solution is measured. The "cholesterol value" of the solution then may be expressed as:

$$CV_s = f(OD)$$

wherein CVs, the solution cholesterol concentration, is calculated as a function of the optical density, OD, when analytical reagents are added to the sample in accordance with testing techniques known or otherwise found to be suitable. The solution sodium concentration, or $Na_s$, may be used to calculate the blood cholesterol level, $CV_b$, in the following manner:

$$CV_b = f(CV_s, Na_s)$$

Numerous other forms of such calculations are possible. For instance, a correction factor (CF) may be determined as a function of the solution's sodium level, wherein:

$$CV_b = f(CV_s, CF)$$

and $$CF = f(Na_s)$$

It is alternatively contemplated that a single apparatus or system may be designed for the calculation of blood analyte levels, wherein an analog or digital electrical signal is generated corresponding to the levels of analyte and normalizing analyte in the solution. For instance, the blood cholesterol number may be calculated as a function of the magnitude of two electrical signals:

$$CV_b = f(E_1, E_2)$$

wherein $E_1$ represents the magnitude of an electrical signal received from a spectrophotometer in measuring optical density for purposes of evaluating total solution cholesterol level and $E_2$ represents the magnitude of an electrical signal received from an electrode specific to sodium.

In actual practice, it is contemplated that numerous variables will affect the results obtained for a given set of specimens. For instance, the readings obtained from an ISE may "wander" from day to day, and the device used to collect the blood or other fluid specimen may contain impurities (such as sodium) that have the potential to introduce errors into the test. For this reason, from time to time a "tare" procedure may be employed. Periodically, a plurality of specimens having a known or measurable analyte level is provided, and from these specimens are prepared modified specimens, the modified specimens being specimens as modified in the manner expected of the unknown specimens. For instance, some number (e.g., six) blood specimens may be periodically placed onto a blood spot collection device similar to those used in the field and dried, followed by elution of the dried samples to form solutions. The solutions are then tested for the level of the analyte and one or more normalizing analytes. From these tests, an algorithm for determining the original fluid analyte level as a function of the measured analyte level and the levels of the normalizing analyte or analytes may be derived. Using this algorithm, modified fluid specimens may be analyzed, wherein the levels of analyte and normalizing analyte may be measured, and the level of analyte in the original specimen may be determined as a function thereof. Errors introduced by impurities (such as sodium) in the collection device will be resolved by this methodology, and errors introduced by factors such as machine calibration will be resolvable with periodic re-calculation of the algorithm. The tare procedure may be performed occasionally or regularly at predetermined intervals (e.g., every day, week, month, or year).

In accordance with the foregoing teaching, the following generalized protocol may be used in determining analyte levels. This protocol assumes that the analyte of interest is a cholesterol and that the normalizing analytes are sodium and chloride.

Calibration of Equipment

Fifteen calibrators and four controls are evaluated. Each "calibrator" is a blood sample of known cholesterol concentration and sodium and chloride concentrations. For each of the calibrators, scalar values X and Y are calculated in accordance with the following equations:

$$Y=(\text{Analyte}-\text{Analyte } RD)/\text{Expected Analyte}$$

$$X=\{E\times 10 \text{ exponent } [\text{Log } 10(E/DC)\times((E \text{ Slope}-FS)/FS]-EBG/EV\}/\text{Expected } E$$

In the foregoing equations, the value "analyte" is the measured analyte concentration, and the value "analyte RD" is the recovery delta. The expected analyte is the known analyte concentration. Value "E" is the measured normalizing analyte (electrolyte) concentration; value "DC" is a drift control value which represents the center of the s-shaped calibration curve and which, for chloride, is 138 mEq/L and for sodium is 5 mEq/L. Value "E Slope" is a calibration slope determined based on the assumption that the normalizing analyte calibration curve is linear. Value "FS," or "Fixed Slope," is a calculated correction factor, which is calculated in accordance with the following equation:

$$\text{Ideal } CL \text{ Slope}=Cl \text{ Slope}*[(\text{Log } 10(CL)-\text{Log } 10(138)]/[\text{Log } 10(\text{Expected } CL)-\text{Log } 10(138)]$$

"Expected E" is the known normalizing analyte concentration Value "EBG" is electrolyte background, and value "EV" is elution volume.

After determination of x and y for each calibrator, scalar values A and B are determined:

$$A = \frac{(\text{sum } y)(\text{sum } x^2) - (\text{sum } x)(\text{sum } xy)}{N(\text{sum } x^2) - (\text{sum } x)^2}$$

$$B = \frac{N(\text{sum } xy) - (\text{sum } x)(\text{sum } y)}{N(\text{sum } x^2) - (\text{sum } x)^2}$$

These variables constitute the results of a regression analysis that provide, A (abscissa intercept) and B (a slope) for the calculation of unknown samples and controls.

Once a calibration has been made, a sodium normalized blood analyte level and a chloride normalized blood analyte level are calculated in accordance with the following equations:

$$\text{Na-Normalized Analyte} = \frac{(\text{Analyte} - \text{Analyte } RD)}{(A1 + B1 \times \{\text{Na} \times 10 \text{ exponent}}$$
$$[\text{Log} 10 \,(\text{Na}/\text{Na } DC) \times$$
$$(\text{Na Slope} - \text{Na } FS)/\text{Na } FS] - \text{Na } BG/EV\}/$$
$$\text{Population Mean Na})$$

$$\text{Cl-Normalized Analyte} = \frac{(\text{Analyte} - \text{Analyte } RD)}{(A2 + B2 \times \{\text{Cl} \times 10 \text{ exponent}}$$
$$[\text{Log} 10 \,(\text{Cl}/\text{Cl } DC) \times$$
$$(\text{Cl Slope} - \text{Cl } FS)/\text{Cl } FS] - \text{Cl } BG/EV\}/$$
$$\text{Population Mean Cl})$$

In these equations, the expected electrolyte value has been replaced by the population electrolyte mean value, which for sodium is 146 mmol/L and for chloride is 107 mmol/L (as measured using this equipment).

Finally, the mean analyte level is determined by calculating the mean average of the sodium normalized blood analyte level and the chloride normalized blood analyte level. It should be appreciated that innumerable variants of the foregoing procedure fall within the purview of the invention.

It is noted that the correction factor for both sodium and for chloride is logarithmically determined, although other non-linear correction factors may be employed. In either case, the calculation may proceed in accordance with the following equations:

$$\text{Na-Normalized Analyte} = \frac{(\text{Analyte} - \text{Analyte } RD)}{(A1 + B1 \times X1)}$$

$$\text{Cl-Normalized Analyte} = \frac{(\text{Analyte} - \text{Analyte } RD)}{(A2 + B2 \times X2)}$$

wherein A and B are scalar values that are calculated as heretofore described or are calculated without accounting for non-linear calibration factors and wherein X1 and X2 are respectively correction values for sodium and for chloride. Values X1 and X2 may be calculated as a linear function of normalizing analyte concentration, as a logarithmic function thereof, or as any other appropriate function.

Figure 2:
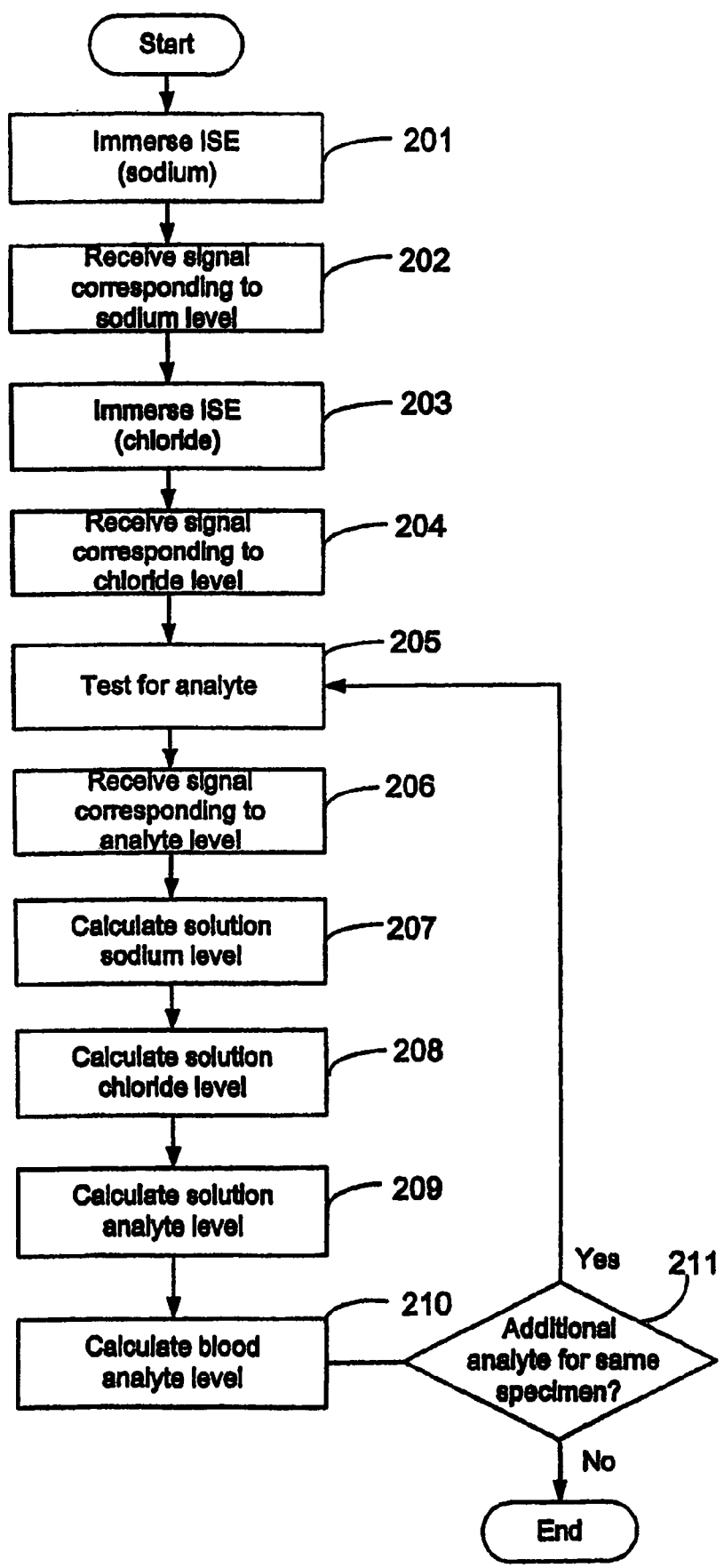
FIG. 2 is a flowchart representing steps in an alternative method for calculating the level of an analyte in blood from which a blood specimen was obtained.

The foregoing exemplary equations and procedures are not meant to be exhaustive but, to the contrary, are intended to illustrate that innumerable variants of the methods for calculating the blood analyte level are included within the scope of the invention. For instance, with respect to FIG. 2, in one such variant, an ISE (sodium) is immersed into an eluted sample at step 201, and a signal corresponding to the sodium level is received at step 202. The signal may be a digital signal, or may be an analog signal, the level of which is recorded. At steps 203 and 204, the same steps are repeated for chloride level, and at steps 205 and 206 respectively, a test for the analyte is performed and a signal is received corresponding to the analyte level. At step 207, the solution sodium level is calculated; at step 208, the chloride level is calculated, and at step 209, the solution analyte level is calculated. At step 210, the blood analyte level is calculated, in this instance based on the magnitude of the solution sodium level, the solution chloride level, and the solution analyte level. If, at step 211, it is desired to test for an additional analyte for the same specimen, control passes to step 205. In such case, if the solution sodium and chloride level have been stored, steps 207 and 208 may be omitted after a signal is received corresponding to the second analyte level. The process may be controlled by any suitable microprocessor or microcontroller (not shown).

Figure 3:
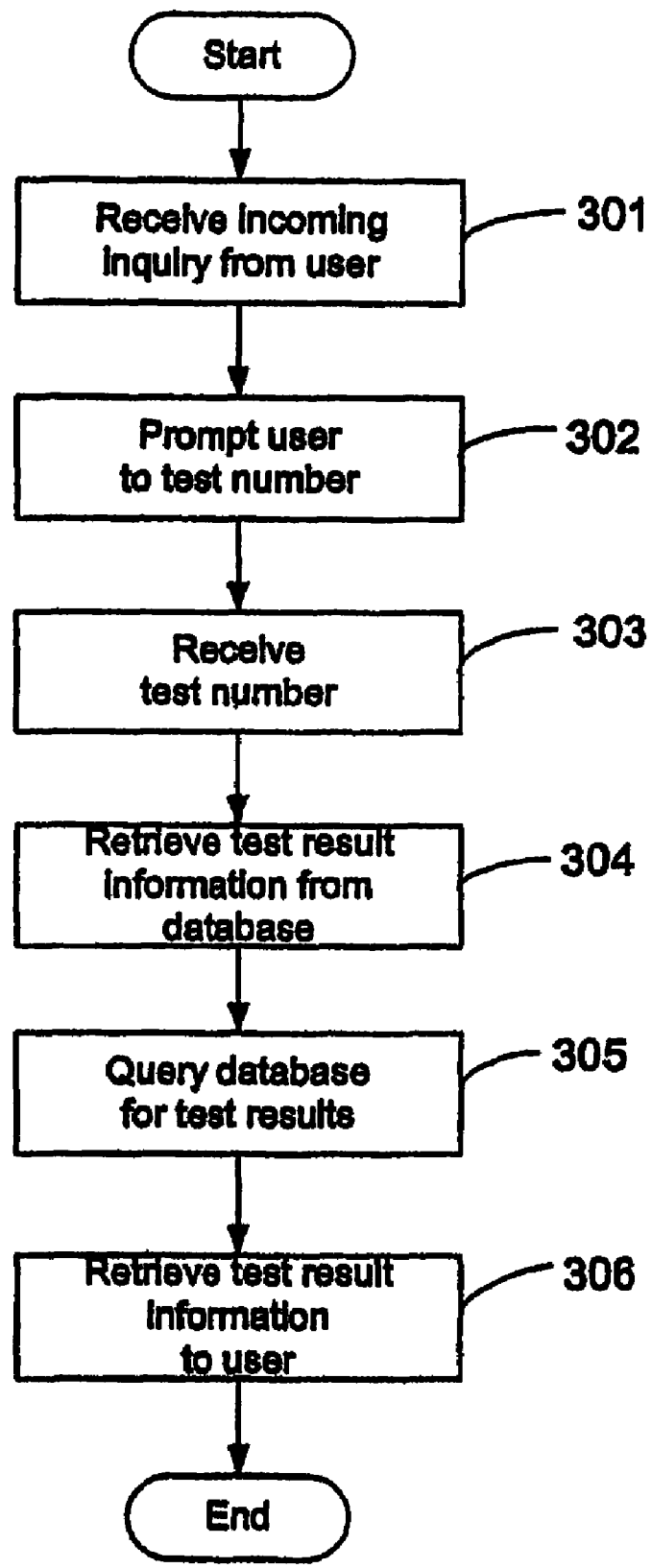
FIG. 3 is a flowchart representing steps in a method for providing test result information to a user.

As stated hereinabove, it is contemplated that the entity who provides test results to a user, who may or may not be the health care professional who has ordered the test, in turn may be the same or different entity from the entity which performs the calculation of the blood analyte level, which in turn may be the same or different entity from the entity which tests the specimen and generates information corresponding to the analyte level or levels and the normalizing analyte level or levels. A very general protocol for a results providing facility is set forth in FIG. 3, wherein an inquiry is received from a user at step 301, and the user is prompted for his or her test number at step 302. At step 303, the test number is received, and at step 304, a test result database is queried for test result information. The information is received at step 305 and is provided to the user at step 306.

Figure 4:
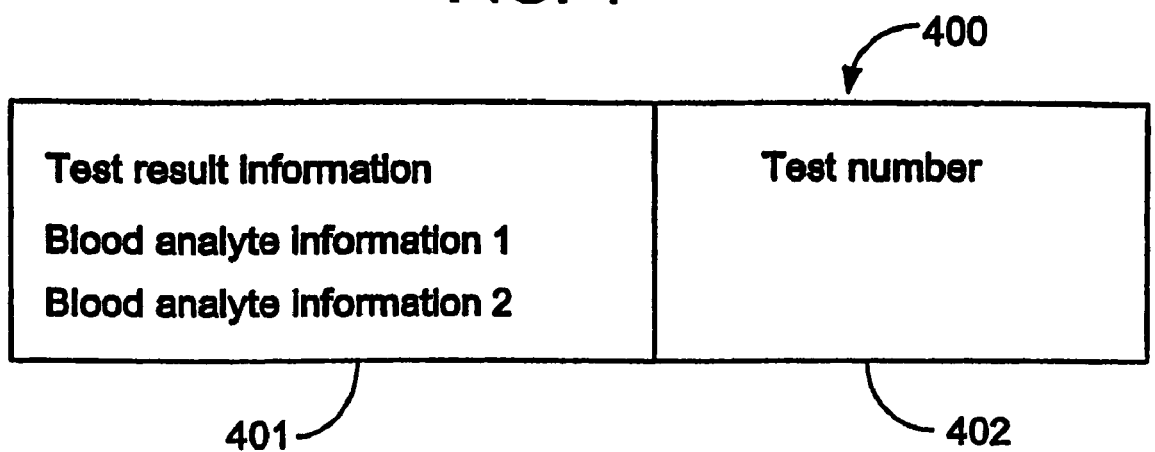
FIG. 4 is a representation of a database record correlating test result information with a test number.

With further reference to FIG. 4, the test result database described above may be structured in any suitable manner. With respect to, for instance, database record 400, the test result information 401, which in the illustrated embodiment includes two items of information, blood analyte information 1 and blood analyte information 2, is correlated with the test number 402. The test number may be an anonymous test number or may be a test number that is associated with a user, for instance, elsewhere in the database record 400 (not shown) or in a different database.

Figure 5:
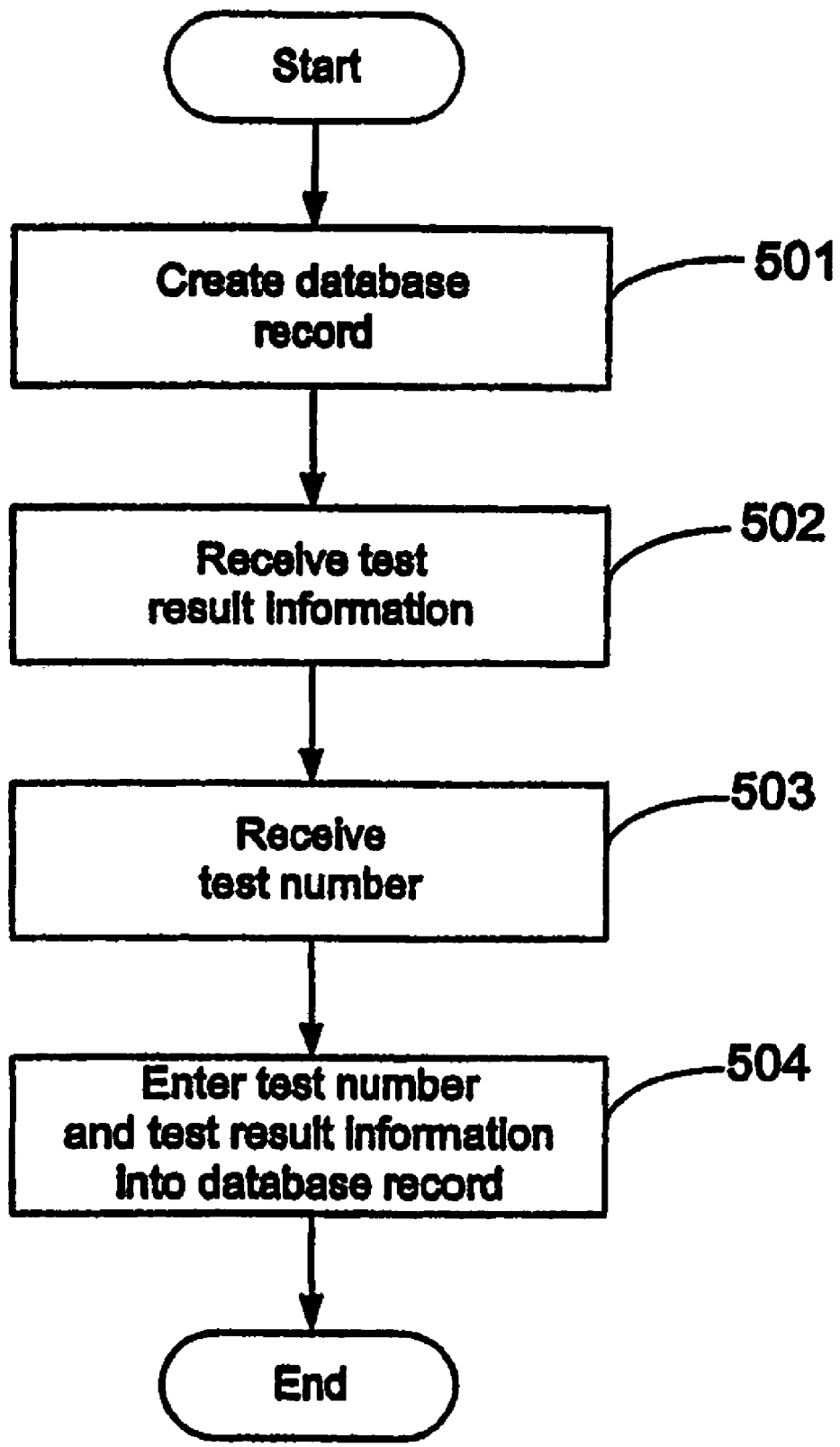
FIG. 5 is a flowchart representing steps in a method for preparing a database of test results and test numbers.

With reference to FIG. 5, the database may be prepared by creating a database record (shown in step 501), receiving test result information and a test number (shown in steps 502 and 503 respectively) and, as shown in step 504, entering the test number and test result information into the database record. More information concerning the role of a results providing facility in a medical or wellness testing protocol can be found in the aforementioned Quattrocchi patents and in copending application Ser. No. 09/709,884.

Figure 6:
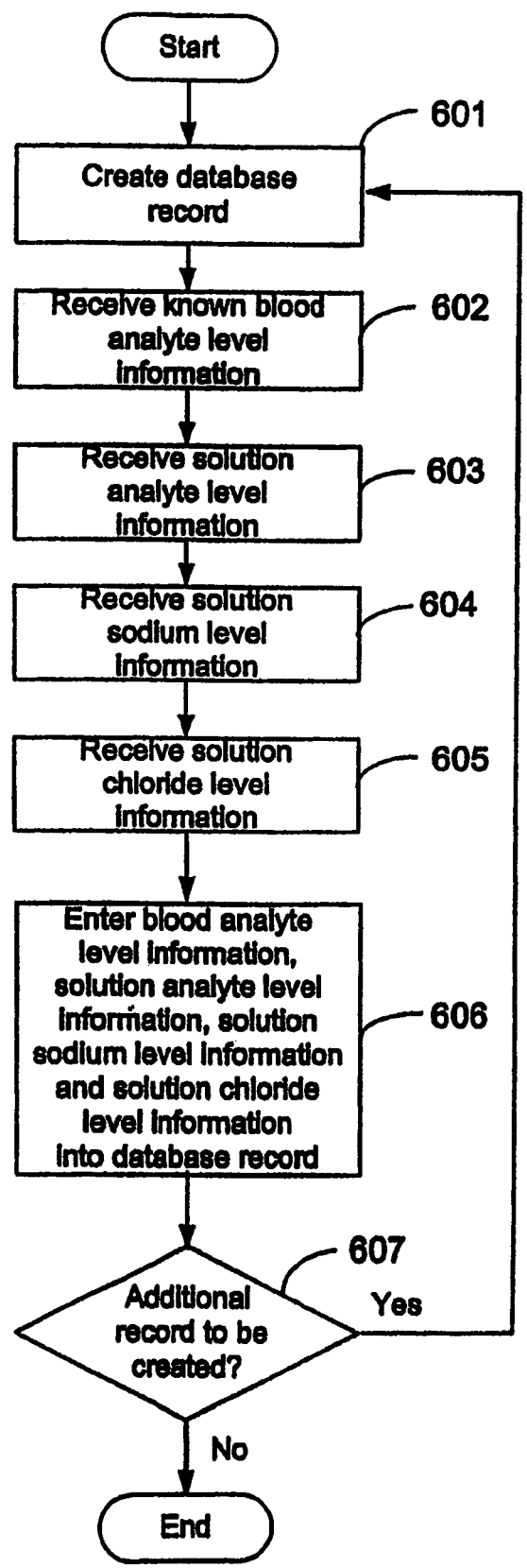
FIG. 6 is a flowchart representing steps in a method for preparing a database of blood analyte levels, solution analyte levels, and solution normalizing analyte levels.
Figure 7:
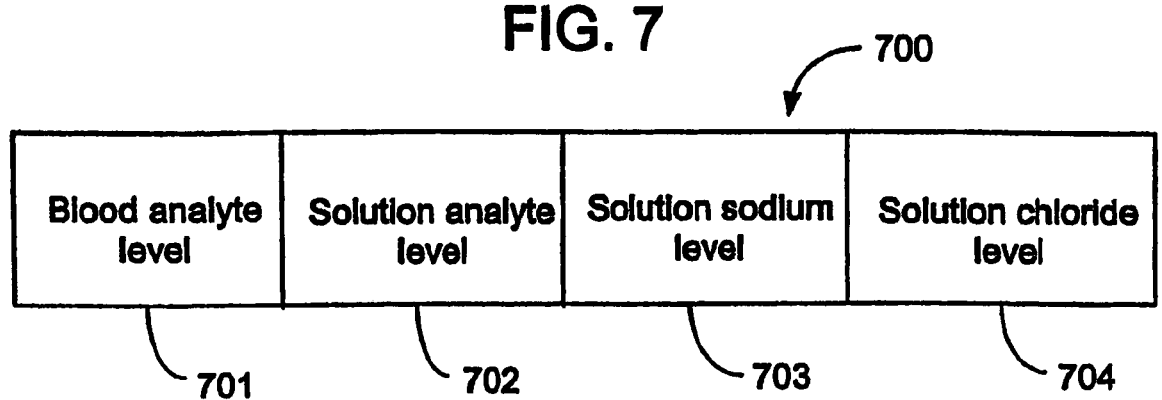
FIG. 7 is a representation of a database record for a database containing blood analyte level information, solution analyte level information and solution normalizing analyte level information.

The invention additionally contemplates a method for preparing a database for use in calculating blood analyte levels. The blood analyte level may be calculated with specific reference to the database, or alternatively the database may be used in conjunction with the preparation of an algorithm for enabling blood level calculation. The database preferably is prepared with reference to blood having a known level of cholesterol or other analyte of interest. Plural specimens of blood having different levels of the analyte are then reduced to an modified specimen, such as a blood spot or serum specimen, and each specimen is analyzed for the analyte of interest and for a normalizing analyte. For instance, with respect to FIG. 6, a database record is created at step 601, and known blood analyte level information is received at step 602. Information as to the solution analyte level and the level of two normalizing analytes, sodium and chloride, for example, are received at steps 603-605, and at step 606, the information received is entered into the database record. If, at step 607, an additional database record is to be created, control passes to step 601, wherein a new database record is created for the new specimen. It should be noted that the order of the steps is not critical, and indeed the database may be prepared sequentially with respect to each blood specimen (i.e., each specimen is reduced to an modified specimen, tested, and the results entered into a database record prior to altering the next specimen of blood), sequentially with respect to database record (wherein all of the blood specimens are reduced to modified specimens prior to entering the first database records) or by any other suitable methodology. A database record 700 as shown in FIG. 7 is thus prepared, with entries 701 through 704 representing respectively blood analyte level, solution analyte, solution sodium level, and solution chloride level.

As discussed above, rather than being calculated, the blood analyte level in a blood fluid specimen may be determined with reference to the database, for instance, by finding the solution analyte level and solution normalizing analyte level or levels in the database that are closest to those of the specimen. Alternatively, any suitable statistical or mathematical technique may be used to derive an algorithm for calculating the blood analyte level from the solution analyte level and at least one normalizing analyte level. In some embodiments, the algorithm is first order with respect at least to the solution analyte level, and may be first order with respect to the solution analyte level and one or both normalizing analyte levels.

Figure 8:
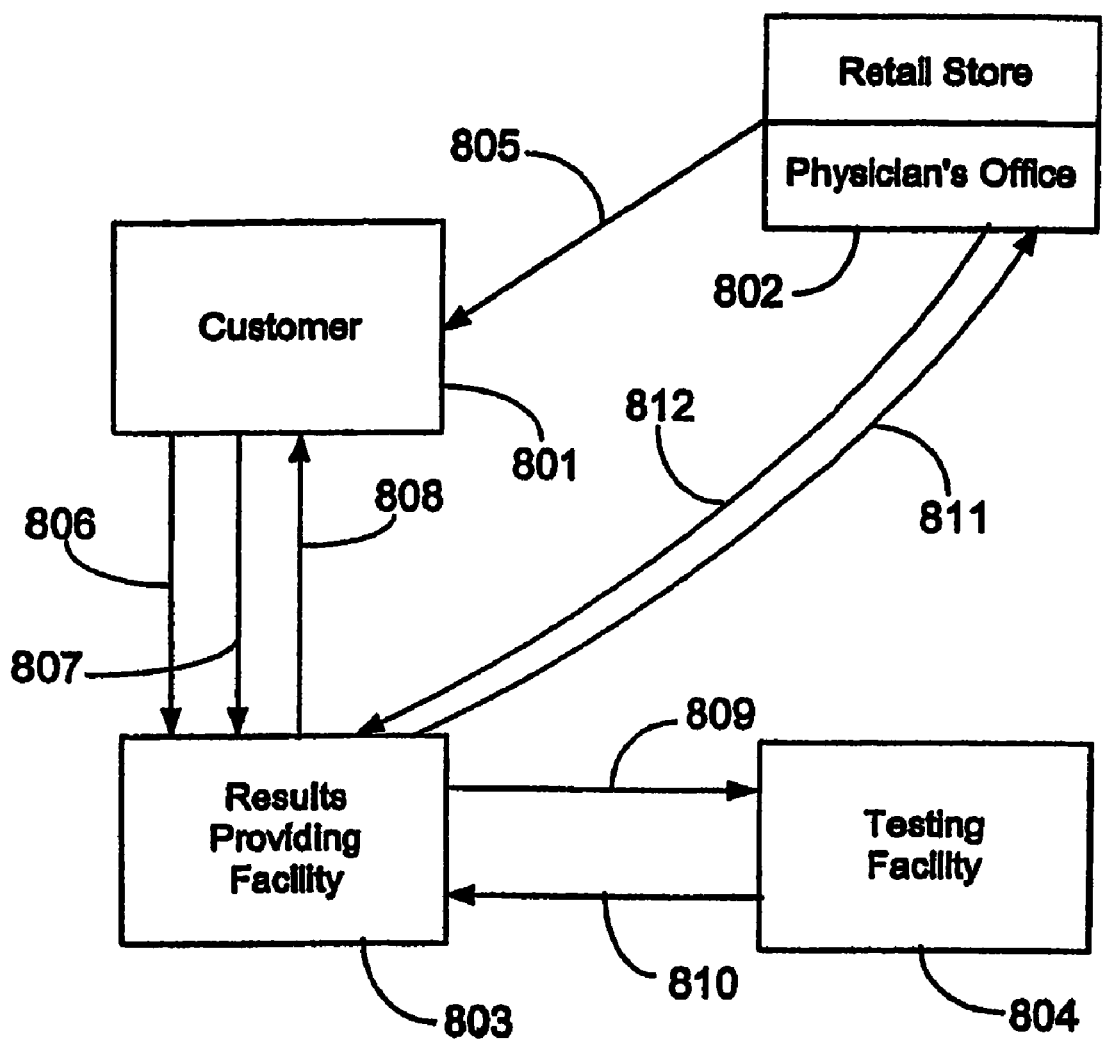
FIG. 8 is a schematic illustration showing various communications between a customer, a results providing facility, and others in connection with a testing protocol.

The invention preferably is conducted in accordance with the general schematic set forth in FIG. 8. Generally the customer 801 purchases a test kit from a physician or retail store 802 (transfer of the kit is shown via transfer communication 805) or in other embodiments a patient is provided with a test kit by or at the direction of a health care provider. The test kit (not shown in FIG. 8) preferably includes instrumentalities for allowing the customer to obtain a blood, serum or serum spot specimen. For instance, as discussed more fully in the aforementioned Quattrocchi patents, the test kit may include a lancet for pricking the user's finger, a blood spot card, or serum spot card, (or the device shown in subsequent figures hereinafter discussed) an informed consent form, and a test number. After preparing the blood, serum or serum spot card, the customer sends the dried blood specimen to a results providing facility 803 as shown via transfer communication 806. In the illustrated embodiment, the results providing facility 803 sends the specimen to a separate testing facility 804, as shown via transfer communication 809. As shown via communication 810, the testing facility provides the test results to the results providing facility. The results may be "raw" results, i.e., results in which the level of the analyte in the blood has not been determined or obtained, or alternatively the testing facility may calculate the blood analyte level and report that result to the results providing facility. As shown at communication 807, the customer contacts the results providing facility, and at communication 808, the results providing facility provides the test results to the customer. Optionally, the results providing facility may be equipped to communicate directly with the physician's office, as shown at communications 811 and 812. Except where transfer of a physical specimen is required, the communication may be made via any means or method now known or hereinafter discovered, for instance, via telephone, wireless communication, electronic mail or "chat" or other electronic communication, or other form of communication.

Figure 9:
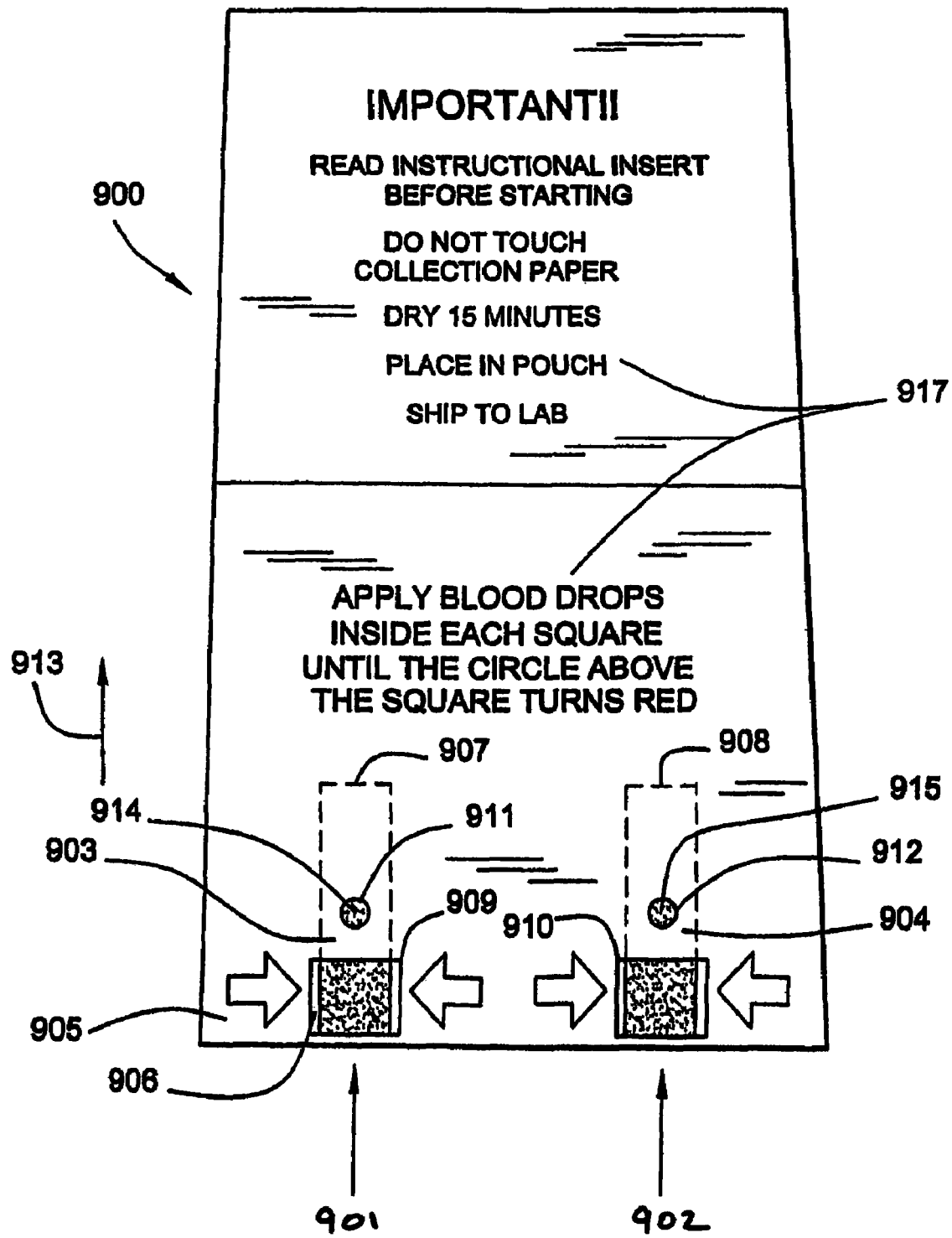
FIG. 9 is a perspective view of the obverse side of a blood collection device useful in conjunction with the invention.
Figure 10:
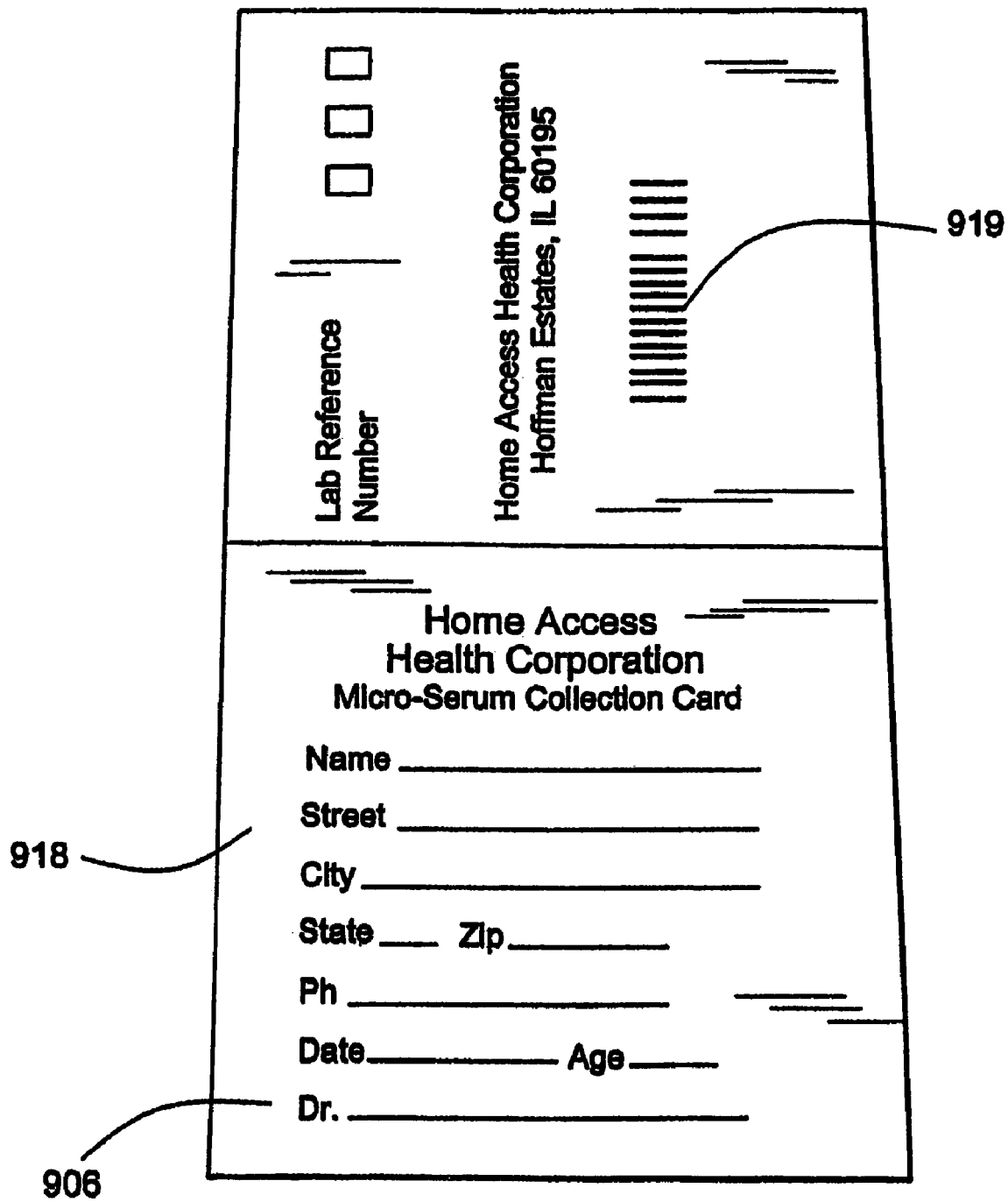
FIG. 10 is a perspective view of the reverse side of the device shown in FIG. 9.

With reference now to FIGS. 9 and 10, the illustrated fluid collection device 900 includes two gangs 901, 901, each comprising a fluid collector 903, 904 that is disposed between a superstrate sheet 905 and a substrate sheet 906 and that is generally fixed with respect to the superstrate sheet 905. The fluid collector is ordinarily connected to the substrate sheet 906 (a portion of which is visible) at one end 907, 908, although the collector may be flexible and thus not entirely fixed with respect to the substrate sheet 905. The substrate is provided with at least one aperture (two shown as 909, 910) by which a user may fluidically transfer blood to the collector. In the illustrated embodiments, secondary apertures 911, 912 are provided. To use the device, a user dispenses blood onto the collector, whereby some or all of the blood wicks in the direction shown by arrow 913 until the portions 914, 915 of the collectors 903, 904 visible through the secondary apertures 914, 915 become tinted, whereupon the user is provided with an indication that sufficient blood has been collected. As illustrated, the device preferably is disposed horizontally relative to the ground during the wicking of blood. Any other suitable indicator that an amount of blood predetermined to be adequate may be provided. In the illustrated embodiments, instructions 917 are provided on the substrate sheet 905 and identification information spaces 918 (shown in FIG. 10) are provided on the substrate sheet 906. The device may be provided with non-textual machine-readable indicia (such as barcode 919) or textual indicia that indicates, for instance, a test number, code number, lot number, or other desired information.

Figure 11:
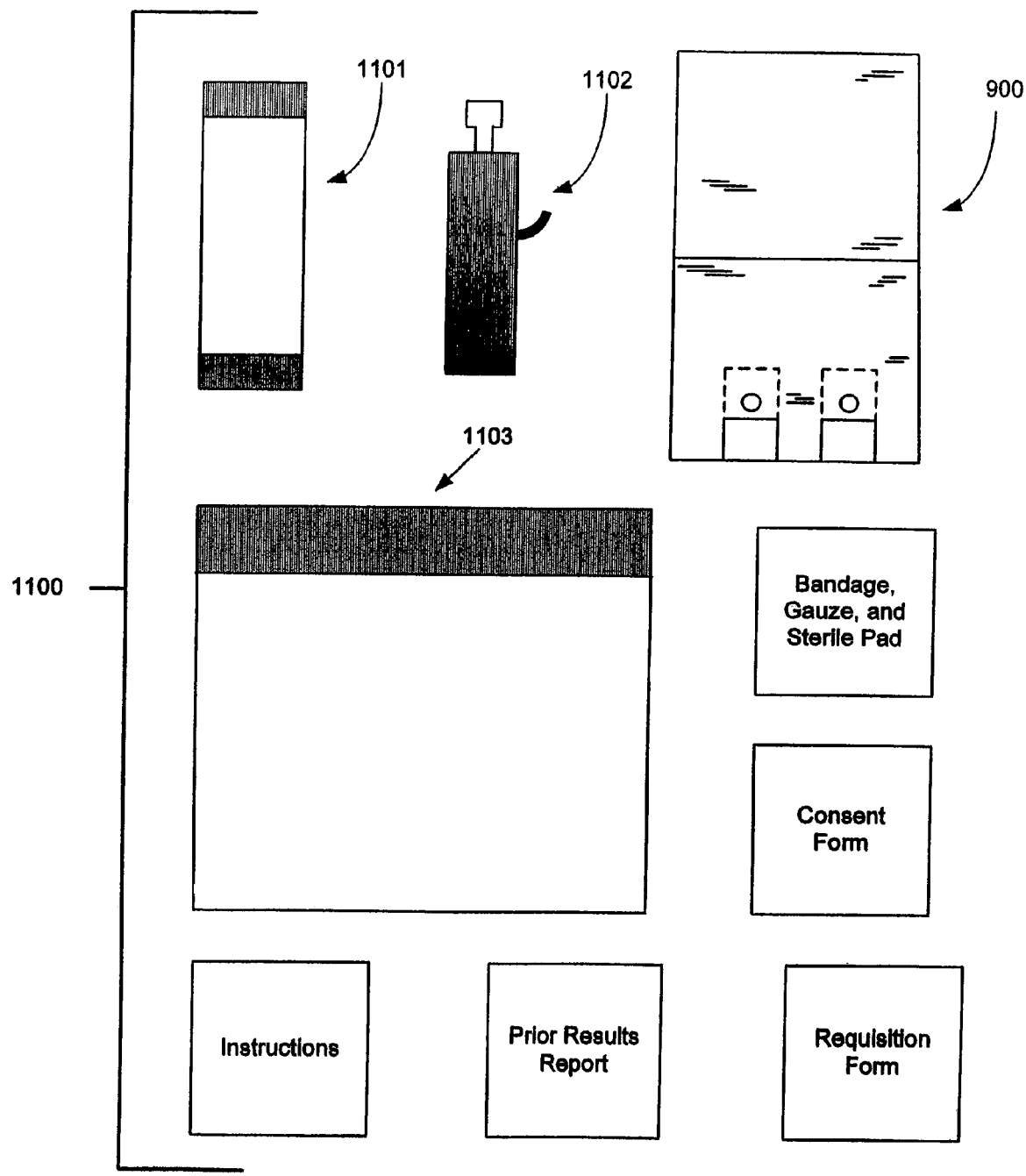
FIG. 11 is a representation of a kit useful in conjunction with the invention.

With reference to FIG. 11, the illustrated kit 1100 includes the specimen collection device 900 illustrated in FIG. 9, and numerous other components, some or none or all of which in practice may be included in a kit. The kit includes a barrier pouch 1103, a desiccant pouch 1104, a lancet 1102, and instruction sheet separate from the kit, a results form from a previous test, and a requisition form as specifically shown in the figure. In preferred embodiments, the kit includes a mailing device, most preferably a preaddressed envelope with postage prepaid for sending the collection device to a testing facility or other appropriate facility. In practice, the kit may further include a bandage, gauze pad, and alcohol pad for use with drawing blood from the patient (not shown) and a form for providing informal consent, which informed consent may be provided anonymously as described in the heretofore mentioned Quattrocchi patents. The barrier pouch should be a pouch that is effective in protecting the dried blood sample during shipping. One suitable barrier material is sold by Caltex Plastics of Vernon, Calif. and comprises a multi-layer barrier film consisting of 25 bleach MG Paper, 48 GA polyester film, 0.0005 aluminum foil, and 0.003 EVA co-polymer, the layers being adhesively bonded together. The pouch preferably is formed with at least one self-sealing device, such as a "zipper" disposed at at least one end of the pouch. A pouch that includes two self-sealing devices, one at each end of the pouch, alternatively may be provided.

The desiccant pouch should be a porous container that includes suitable desiccant effective to provide a desiccating protective effect on a blood fluid specimen, and to some extent to protect the integrity of the collection device during transport to the physician or patient. Any suitable desiccant material may be used in conjunction with the invention. One suitable desiccant is made by SudChemie of Balen, N.Mex. under part number 4286. This material comprises silica and clay disposed in admixture in a 5 gram pouch. Any other suitable desiccant may be used in conjunction with the invention.

Figure 15:
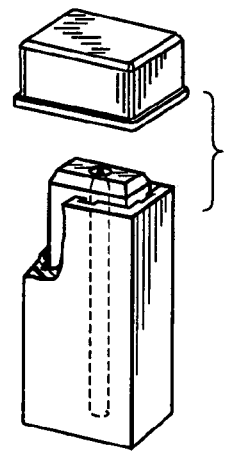
FIG. 15 is an exploded view of a lancet useful in conjunction with preferred embodiments of the invention.

Likewise, any suitable lancet may be employed in conjunction with the invention. The illustrated lancet 1102 preferably comprises a blood-obtaining lancet such as that presently available from Palco Labs of Santa Cruz, Calif. as the EZ-LETS II or the larger lancet shown in FIG. 15. These devices are a single-use lancet that are spring-loaded to enable the lancet to sharply pierce a user's skin. Any other suitable lancet may be used in conjunction with the invention. The barrier film pouch is sized to receive the fluid collection device. Preferably, the pouch is sized to receive the desiccant pouch and the fluid collection device.

Figure 12:
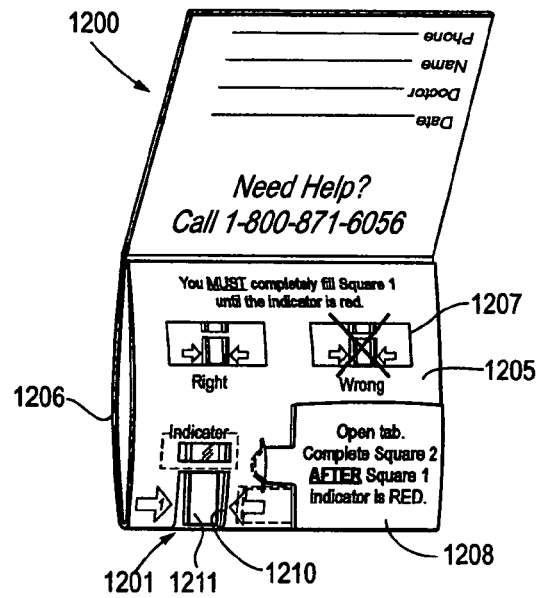
FIG. 12 is a perspective view of the obverse side of alternative embodiment of a two-gang blood collection device in accordance with an embodiment of the invention, shown prior to use with one gang covered.
Figure 13:
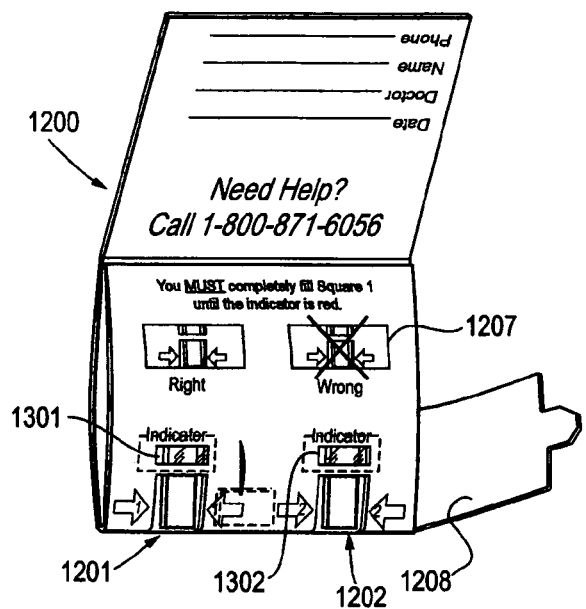
FIG. 13 is a perspective view of the obverse side of the blood collection device shown in FIG. 12, shown with the second gang exposed.

An alternative embodiment of a fluid collection device 1200 suitable for use in conjunction with the invention includes two gangs 1201, 1202 (gang 1202 not shown in FIG. 12). Each of the gangs comprises a fluid collector that is disposed between a superstrate sheet 1205 and a device substrate sheet 1206 (best shown in FIG. 14) and wherein each fluid collector is generally fixed with respect to the superstrate sheet 1205. The fluid collectors are ordinarily connected to the substrate sheet at one end of the substrate sheet. In the embodiment illustrated in FIGS. 12-14, usage instructions 1207 are provided on a portion of the collector, the usage instructions including an illustration as to proper and improper blood filling profiles.

The collector 1200 includes a tab cover 1208 that releasably covers one of the gangs 1202. In ordinary use, the fluid collector is provided in a form such that the cover is closed. The user dispenses blood through a first aperture 1210 in the first gang 1201 onto collector 1211, and, after the fluid collector becomes sufficiently filled, the user opens the cover and repeats the dispensation of blood onto the second gang 1202. Instructions to this effect are provided.

Each gang is provided with a second pair of apertures 1301, 1302, and, in accordance with this embodiment of the invention, each of the second apertures is provided with a window 1303, 1304. The window allows for a visual indication as to fluid flow across the collectors but the window inhibits blood flow through the second apertures 1301, 1302.

Figure 14:
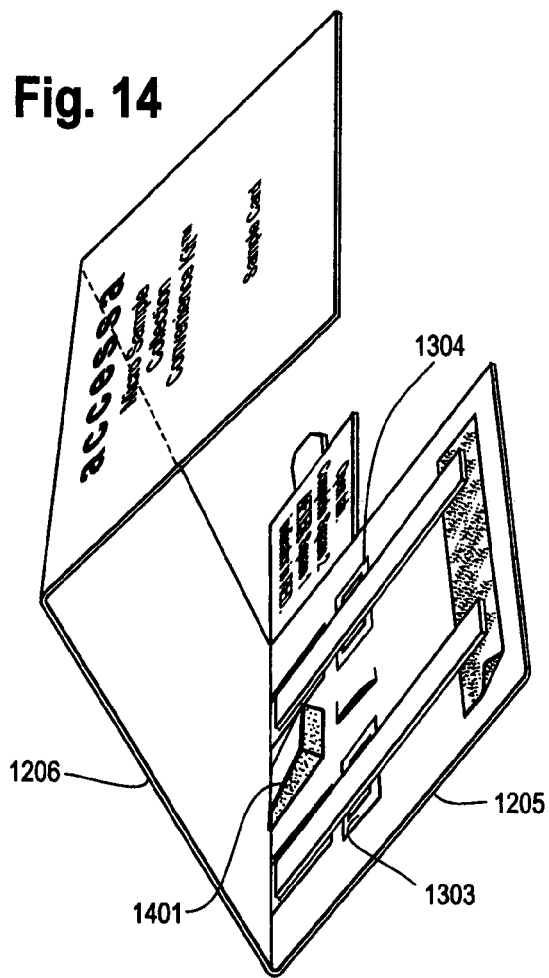
FIG. 14 is a side perspective view of the blood collection device shown in FIGS. 12 and 13, partially opened to show internal details.

With particular reference to FIG. 14, the device is provided with a spacer 1401 disposed between the substrate and superstrate sheets 1205, 1206 and which inhibits a contact of at least a portion of the substrate and superstrate sheets. In this embodiment of the invention, the substrate and superstrate sheets preferably are formed of a fluid-resistant, laminated cardstock. In accordance with the heretofore described construction, blood is inhibited from leaking off of the fluid collectors onto the cardstock, and the presence of the spacer allows for a small air gap between the substrate and superstrate sheets to thereby assist in blood drying. As heretofore described with respect to other embodiments of the invention, the device may be provided with non-textural machine-readable indicia, such as a bar code, or textual indicia that indicates, for instance, a test number, code number, lot number, or other desired information.

An instruction set may be included as a separate sheet within the kit, or alternatively the instructions may be integral with (for example, imprinted on) the fluid collection device. The kit may further include results from a previous test. Such is useful, for example, in the case of patients who require periodic testing, for instance, of blood cholesterol. The invention encompasses in some embodiments a method of providing a test kit and test results to a health care provider and/or a patient, the test results being results from a previous test and the test kit being a kit as heretofore described. In some embodiments, the patient responds to an indication in the results form as to whether or when to obtain a subsequent blood sample or other type of sample.

The invention contemplates methods wherein a physician is provided with a test kit as heretofore described and wherein the patient's blood is drawn at the direction of the physician or other health care provider, either at the premises of the health care provider or elsewhere without the healthcare provider being present. In keeping with these embodiments, the kit may include a requisition form, the requisition form permitting indication of the type of test or tests to be conducted on the fluid to be collected by the device. In some embodiments, the requisition form lists a plurality of test types, and the healthcare provider need only indicate (such as with a check mark) the type of test desired. On any such form, space may be indicated for the health care provider to indicate any other sort of test desired to be conducted.

In a highly preferred embodiment of the invention, the fluid collector is an absorbent paper or glass fiber substrate that is coated with a saccharide, preferably a mono or di-saccharide and most preferably xylose. The saccharide should be present in contact with the substrate in an amount effective to inhibit triglycerides ordinarily present in the expected blood sample from binding to the fiber matrix. The substrate should be one that permits at least substantial separation of the red blood cell component of blood cells from other portions of the blood (i.e., serum). It is believed that the saccharide component permits more effective recovery of the serum components from the substrate sheet. The substrate may be coated only at the surface on one or both sides with the saccharide, but preferably the substrate is coated on internal surfaces as well as on the exterior surface. In one embodiment, 180 µl of a 5% solution of xylose is applied to the internal surface of the 0.8×7 cm substrate (such that substantially all of the substrate is wetted) and allowed to air dry. If the fluid collector is used in the device shown in FIGS. 9 and 10, the blood cells will remain near the end of the collection device (opposite the direction of arrow 913) while the serum will wick toward the other end of the card. Upon receipt by a testing laboratory, a portion of the fluid collector may be excised and eluted. Preferably, the excised portion includes a portion of the collector "above" the terminal wicking point of the serum. It has been found that using a two-gang device as described herein, if one or both of the fluid collectors are deemed to have been filled inadequately, one-half of each fluid collector may be excised and eluted. One commercial product (Whatman GF/AVA paper) contains sodium, and it is believed that by excising filter paper above the terminal wicking point a consistent amount of sodium will be introduced into the eluted fluid. The device may be prepared by applying a solution of the saccharide to the substrate.

The glass fiber paper heretofore described comprises a mat of glass fibers that are at least substantially coated with polyvinyl alcohol. The fibers define a plurality of pores that have a pore size that, in preferred embodiments of the invention, is effective to at least substantially prevent lysing of red blood cells while permitting at least substantial separation of serum from red blood cells via differential wicking. Any suitable substrate that provides such a pore size and that permits such substantial separation in the absence of blood cell lysing may be used in conjunction with the invention. Preferably, the average pore size defines a fluid removal rating, as this term is used in conjunction with filtration technology, of 1.7 micron.

The invention enables venous blood analyte levels to be determined from capillary blood specimens. It is contemplated that in most embodiments the solution analyte level will be normalized to the venous blood level of the analyte, but it is also contemplated that the solution value may be normalized to capillary blood level (or for that matter a different blood level).

The databases discussed herein may be created and stored as computer files on a computer readable medium, such as a diskette, hard disk, CD-ROM, DVD-ROM, ROM chip or EPROM chip, or any other suitable medium as may be now known or hereinafter discovered. The tests for the analyte and normalizing analytes may be performed by any conventional or otherwise suitable technique now or hereinafter found to be suitable, and likewise the analyte and normalizing analyte (which may be discrete atoms, ions, compounds, biochemical materials, or properties) may be those specifically described herein or others as may be found suitable for use in conjunction with the invention.

The following examples are provided to illustrate the invention, but should not be construed as limiting the invention in scope unless otherwise indicated. Unless otherwise indicated in these examples, the measured analyte level was corrected using sodium as the sole normalizing analyte. The correction was made using a simple linear regression. It should be understood that more complex single variable and multivariate regressions may be used in conjunction with the invention, and thus the statistical techniques employed in these examples should be viewed as non-limiting.

EXAMPLE 1

This example demonstrates the performance of the invention in the measurement of total cholesterol.

Fifteen patients were used to obtain blood specimens (micro-serum specimens) via venal puncture. Serum from each specimen was spotted and dried on filter paper with applied volumes ranging from approximately 8 to 16 µl. The number of spots for each blood specimen is listed in the column "No." in the table below. Each spot was eluted and measured for cholesterol and sodium. For each specimen for each patient, the normalized cholesterol level was calculated based on the level of a measured analyte in the fluid (cholesterol) and a normalizing analyte (sodium). The normalized cholesterol level was obtained according to the present invention using linear regression techniques to yield the following function: Normalized Cholesterol=Measured Cholesterol/((−0.003306)+0.9781×(Measured Sodium/13)), where 139 (mEq/L) is the population mean for sodium. The regression was calculated based on five direct measurements of the cholesterol level from the same blood sample, as listed in the column "Mean Serum Cholesterol." The mean average of the normalized cholesterol values for each patient is given in the column "mean normalized cholesterol" and the coefficient of variation of the normalized cholesterol levels obtained for each patient is listed in the column designated "Normalized Cholesterol CV %."

| Patient | No. | Mean Serum Cholesterol | Mean Normalized Cholesterol | Normalize Cholesterol CV % |
|---|---|---|---|---|
| A | 11 | 152.35 | 153.68 | 3.85 |
| Ja | 12 | 165.79 | 162.50 | 1.42 |
| Il | 14 | 180.93 | 180.47 | 4.61 |
| Ca | 12 | 186.20 | 182.28 | 0.70 |
| Br | 10 | 187.06 | 185.35 | 2.93 |
| Mi | 12 | 187.14 | 186.21 | 1.85 |
| Gr | 12 | 187.42 | 189.14 | 1.65 |
| Ed | 12 | 200.38 | 197.18 | 1.36 |
| Tr | 11 | 220.83 | 221.89 | 2.00 |
| Bb | 11 | 232.65 | 233.06 | 1.89 |
| Ma | 11 | 236.73 | 245.53 | 1.02 |
| Jo | 11 | 237.37 | 237.24 | 1.95 |
| JJ | 14 | 262.41 | 259.24 | 1.75 |
| Kt | 12 | 264.30 | 268.23 | 1.86 |
| TT | 13 | 269.36 | 273.53 | 2.79 |

A comparative linear regression was generated for the data points collected in this Example. The linear fit followed the following equation:

Mean Normalized Cholesterol=−7.97+1.04×Mean Serum Cholesterol, with the correlation coefficient, expressed as $R^2$, being greater than 0.99.

EXAMPLE 2

This example demonstrates the performance of the invention in the measurement of HDL.

The same dried spots from the same fifteen patients in Example 1 were used to obtain a measured value for HDL. The normalized HDL level was obtained according to the present invention using linear regression techniques yielding the following function:

Normalized HDL=HDL/(0.0158+1.060×(Sodium/139)). The following data was measured or calculated in the same manner as in Example 1.

| Patient | No. | Mean Serum HDL | Mean Normalized HDL | Normalized HDL CV % |
|---|---|---|---|---|
| Il | 14 | 45.77 | 47.03 | 2.35 |
| A | 11 | 46.05 | 47.77 | 2.17 |
| Jo | 11 | 47.40 | 48.50 | 2.12 |
| Ja | 12 | 48.87 | 53.22 | 2.23 |
| JJ | 14 | 49.07 | 48.15 | 1.68 |
| Gr | 12 | 49.64 | 52.45 | 1.62 |
| Mi | 12 | 59.96 | 58.95 | 1.69 |
| Br | 10 | 57.20 | 55.83 | 2.66 |
| Ed | 12 | 71.00 | 71.09 | 0.92 |
| Kt | 12 | 73.08 | 72.46 | 1.53 |
| TT | 13 | 76.16 | 75.77 | 2.27 |
| Ca | 12 | 78.01 | 75.93 | 1.50 |
| Bb | 11 | 78.77 | 73.35 | 1.99 |
| Ma | 11 | 87.84 | 84.75 | 0.94 |
| Tr | 11 | 91.15 | 86.42 | 1.46 |

A comparative linear regression was generated for the data points collected in this Example. The linear fit followed the following equation:

Mean Normalized HDL=8.15+0.87×Mean Serum HDL, with the correlation coefficient, expressed as $R^2$, being greater than 0.99.

EXAMPLE 3

This example demonstrates the performance of the invention in the measurement of triglycerides (TG).

The same dried spots from the same fifteen patients in Example 1 were used to obtain a measured value for TG. The normalized TG level was obtained according to the present invention using linear regression techniques yielding the following function:

Normalized $TG=TG$/((−0.0136)+0.9307×(Sodium/139)). The following data was measured or calculated in the same manner as in Example 1.

| Patient | No. | Mean Serum TG | Mean Normalized TG | Normalized TG CV % |
|---------|-----|---------------|--------------------|--------------------|
| Ca | 12 | 37.63 | 38.76 | 1.95 |
| Bb | 11 | 46.86 | 48.55 | 1.75 |
| A | 11 | 48.75 | 50.16 | 2.73 |
| Ja | 12 | 49.68 | 49.94 | 3.31 |
| Kt | 12 | 52.15 | 48.19 | 1.32 |
| Br | 10 | 55.00 | 56.56 | 4.14 |
| Ma | 11 | 56.05 | 56.40 | 2.03 |
| Il | 14 | 59.09 | 60.88 | 6.22 |
| Ed | 12 | 62.91 | 61.65 | 1.25 |
| Tr | 11 | 66.69 | 67.66 | 1.63 |
| TT | 13 | 68.76 | 72.14 | 13.37 |
| Mi | 12 | 71.84 | 72.63 | 1.62 |
| Jo | 11 | 109.28 | 107.10 | 2.27 |
| JJ | 14 | 117.31 | 112.24 | 5.03 |
| Gr | 12 | 139.47 | 136.74 | 2.13 |

A comparative linear regression was generated for the data points collected in this Example. The linear fit followed the following equation:

Mean Normalized $TG = 3.36 + 0.95 \times$ Mean Serum $TG$, with the coefficient, expressed as $R^2$, being greater than 0.995.

EXAMPLE 4

This example demonstrates the performance of the invention in the measurement of LDL. The same observations from the same fifteen patients in Example 1, 2 and 3 were used to calculate a value for LDL in serum and a value for LDL in MSS according to the Friedewald formula:

Mean Serum LDL = Mean Serum Cholesterol − Mean Serum HDL − Mean Serum $TG/5$

Mean Normalized LDL = Mean Normalized Cholesterol − Mean Normalized HDL − Mean Normalized $TG/5$, respectively.

The following data was calculated (mean serum LDL was calculated from the mean values reported in Examples 1-3)

| Patient | No. | Mean Serum LDL | Mean Normalized LDL | Normalized LDL CV % |
|---------|-----|----------------|---------------------|---------------------|
| A | 11 | 96.55 | 95.30 | 5.36 |
| Ca | 12 | 100.66 | 98.82 | 1.17 |
| Ja | 12 | 106.98 | 99.22 | 2.32 |
| Gr | 12 | 109.88 | 109.00 | 2.19 |
| Mi | 12 | 115.81 | 112.90 | 2.80 |
| Tr | 11 | 116.35 | 121.21 | 3.11 |
| Ed | 12 | 116.80 | 113.76 | 1.98 |
| Br | 10 | 118.86 | 118.21 | 3.23 |
| Il | 14 | 123.34 | 119.75 | 5.72 |
| Ma | 11 | 137.68 | 149.45 | 1.72 |
| Bb | 11 | 144.51 | 150.01 | 2.12 |
| Jo | 11 | 168.11 | 167.55 | 2.66 |
| Tt | 13 | 179.45 | 183.33 | 3.33 |
| Kt | 12 | 180.78 | 186.13 | 2.19 |
| JJ | 14 | 189.88 | 189.54 | 1.89 |

A comparative linear regression was generated for the data points collected in this Example. The linear fit followed the following equation:

Mean Normalized $LDL = -8.16 + 1.07 \times$ Mean Serum $LDL$, with the correlation, expressed as $R^2$, being equal to 0.98.

EXAMPLE 5

This example demonstrates the performance of the invention in the measurement of total cholesterol.

One hundred thirty-two patients were used to obtain blood via venal puncture (venous blood specimens) and by pricking their fingers (capillary blood specimens). Capillary blood was spotted on xylose-coated Whatman GF/AVA filter paper, using a device similar to that shown in FIG. 9. Capillary blood specimens were dried and the portion of the filter paper which contained separated serum was cut out and eluted. Eluate from each specimen was measured for cholesterol and sodium. The normalized cholesterol level was obtained according to the present invention using a variable formula: Normalized Cholesterol = Measured Cholesterol/$(A+B \times$ (Measured Sodium/139)). In this equation, A and B were scalar values that were periodically recalculated based on the "tare" procedure heretofore described, whereby a regression for six patients was calculated and the A and B values from this regression were used to calculate normalized cholesterol values for specimens analyzed before the next tare period. Actual (directly measured in venous blood) and calculated normalized cholesterol valves for these patients are given below.

| Patient | Serum Cholesterol | Normalized Cholesterol |
|---------|-------------------|------------------------|
| 1 | 172.68 | 157.54 |
| 2 | 149.25 | 154.61 |
| 3 | 176.81 | 175.60 |
| 4 | 189.78 | 187.41 |
| 5 | 170.38 | 173.03 |
| 6 | 189.67 | 188.80 |
| 7 | 130.52 | 128.80 |
| 8 | 266.76 | 276.31 |
| 9 | 151.29 | 152.49 |
| 10 | 219.86 | 211.23 |
| 11 | 242.00 | 251.07 |
| 12 | 232.41 | 230.66 |
| 13 | 173.09 | 176.48 |
| 14 | 190.89 | 190.86 |
| 15 | 264.47 | 260.46 |
| 16 | 236.18 | 244.49 |
| 17 | 272.58 | 279.76 |
| 18 | 240.29 | 228.83 |
| 19 | 169.32 | 166.57 |
| 20 | 192.02 | 195.03 |
| 21 | 239.83 | 235.33 |
| 22 | 225.13 | 225.13 |
| 23 | 169.40 | 156.05 |
| 24 | 197.93 | 183.67 |
| 25 | 151.59 | 146.26 |
| 26 | 235.43 | 247.88 |
| 27 | 178.84 | 170.79 |
| 28 | 196.40 | 191.34 |
| 29 | 240.99 | 230.52 |
| 30 | 171.53 | 173.95 |
| 31 | 229.43 | 229.43 |
| 32 | 217.54 | 223.84 |
| 33 | 187.23 | 183.58 |
| 34 | 175.68 | 173.95 |
| 35 | 174.69 | 172.34 |
| 36 | 251.23 | 249.20 |
| 37 | 203.70 | 185.98 |
| 38 | 123.30 | 114.96 |
| 39 | 136.04 | 127.97 |
| 40 | 251.33 | 243.27 |
| 41 | 216.14 | 218.02 |
| 42 | 145.14 | 156.86 |
| 43 | 208.58 | 203.43 |
| 44 | 250.25 | 245.07 |
| 45 | 235.76 | 250.40 |
| 46 | 193.19 | 187.83 |
| 47 | 211.75 | 223.38 |

-continued

| Patient | Serum Cholesterol | Normalized Cholesterol |
|---|---|---|
| 48 | 221.15 | 226.04 |
| 49 | 199.41 | 196.35 |
| 50 | 249.35 | 259.44 |
| 51 | 166.46 | 165.63 |
| 52 | 154.64 | 151.56 |
| 53 | 187.36 | 190.37 |
| 54 | 256.78 | 260.40 |
| 55 | 230.59 | 222.39 |
| 56 | 208.57 | 224.14 |
| 57 | 183.92 | 181.28 |
| 58 | 159.73 | 156.20 |
| 59 | 155.31 | 153.59 |
| 60 | 205.29 | 197.61 |
| 61 | 204.49 | 198.97 |
| 62 | 219.21 | 221.45 |
| 63 | 122.83 | 114.88 |
| 64 | 175.13 | 176.48 |
| 65 | 201.35 | 211.70 |
| 66 | 216.66 | 209.09 |
| 67 | 227.50 | 231.96 |
| 68 | 151.28 | 153.23 |
| 69 | 130.10 | 128.40 |
| 70 | 175.95 | 173.45 |
| 71 | 182.38 | 183.21 |
| 72 | 201.03 | 195.89 |
| 73 | 175.86 | 189.73 |
| 74 | 146.10 | 149.88 |
| 75 | 116.17 | 103.88 |
| 76 | 193.58 | 197.59 |
| 77 | 291.91 | 296.11 |
| 78 | 184.93 | 185.49 |
| 79 | 145.82 | 141.34 |
| 80 | 182.73 | 180.78 |
| 81 | 175.84 | 170.03 |
| 82 | 148.99 | 151.67 |
| 83 | 212.79 | 213.40 |
| 84 | 228.82 | 225.39 |
| 85 | 218.44 | 229.26 |
| 86 | 169.43 | 173.84 |
| 87 | 151.43 | 157.96 |
| 88 | 217.96 | 218.63 |
| 89 | 239.39 | 244.11 |
| 90 | 148.62 | 152.86 |
| 91 | 136.81 | 132.60 |
| 92 | 119.13 | 113.31 |
| 93 | 121.10 | 119.61 |
| 94 | 165.31 | 163.34 |
| 95 | 111.65 | 132.34 |
| 96 | 190.25 | 184.44 |
| 91 | 201.78 | 206.49 |
| 98 | 133.26 | 137.69 |
| 99 | 225.84 | 221.61 |
| 100 | 244.66 | 230.25 |
| 101 | 164.72 | 168.10 |
| 102 | 150.75 | 146.82 |
| 103 | 163.51 | 110.41 |
| 104 | 196.06 | 198.89 |
| 105 | 213.32 | 206.01 |
| 106 | 186.62 | 183.13 |
| 107 | 163.46 | 162.71 |
| 108 | 244.58 | 250.24 |
| 109 | 231.82 | 231.32 |
| 110 | 171.94 | 172.27 |
| 111 | 201.12 | 209.36 |
| 112 | 205.41 | 209.00 |
| 113 | 157.54 | 156.02 |
| 114 | 191.41 | 190.59 |
| 115 | 192.20 | 197.31 |
| 116 | 193.52 | 183.12 |
| 117 | 257.83 | 248.49 |
| 118 | 178.32 | 171.44 |
| 119 | 203.64 | 209.32 |
| 120 | 210.36 | 230.29 |
| 121 | 207.14 | 220.04 |
| 122 | 200.05 | 205.38 |
| 123 | 216.34 | 219.09 |
| 124 | 190.10 | 179.14 |

-continued

| Patient | Serum Cholesterol | Normalized Cholesterol |
|---|---|---|
| 125 | 293.34 | 272.48 |
| 126 | 228.57 | 226.02 |
| 127 | 111.60 | 174.88 |
| 128 | 142.80 | 148.94 |
| 129 | 197.16 | 205.05 |
| 130 | 220.50 | 218.43 |
| 131 | 220.32 | 231.50 |
| 132 | 255.18 | 255.23 |

A comparative linear regression was generated for the data points collected in this Example. The linear fit followed the following equation:

Normalized Cholesterol=−1.16+1.00×Serum Cholesterol, with the correlation coefficient, expressed as $R^2$, being 0.966.

EXAMPLE 6

This example demonstrates the performance of the invention in the measurement of HDL. The dried spots and venous blood specimens from the same one hundred thirty-two patients in Example 5 were used to measure HDL in capillary blood and compare it to a measured value for HDL in venous blood. The normalized HDL level in capillary blood was obtained according to the present invention using a formula: Normalized HDL=Measured HDL/(A+B×(Measured Sodium/139)), where A and B were obtained as previously described. The following results were observed.

| Patient | Serum HDL | Normalized HDL |
|---|---|---|
| 1 | 58.90 | 61.12 |
| 2 | 41.28 | 42.33 |
| 3 | 38.54 | 39.15 |
| 4 | 48.84 | 46.19 |
| 5 | 61.56 | 54.98 |
| 6 | 52.68 | 48.79 |
| 7 | 47.69 | 45.15 |
| 8 | 34.69 | 39.49 |
| 9 | 57.45 | 56.32 |
| 10 | 38.00 | 36.33 |
| 11 | 47.53 | 42.14 |
| 12 | 60.04 | 58.94 |
| 13 | 36.08 | 37.35 |
| 14 | 46.09 | 48.37 |
| 15 | 42.22 | 42.82 |
| 16 | 34.70 | 38.98 |
| 17 | 55.76 | 55.79 |
| 18 | 21.16 | 24.53 |
| 19 | 55.33 | 55.69 |
| 20 | 44.66 | 42.65 |
| 21 | 83.26 | 81.00 |
| 22 | 44.33 | 46.14 |
| 23 | 40.71 | 40.69 |
| 24 | 47.24 | 43.98 |
| 25 | 49.46 | 47.71 |
| 26 | 44.37 | 43.30 |
| 27 | 50.16 | 48.34 |
| 28 | 55.49 | 61.30 |
| 29 | 58.90 | 61.12 |
| 30 | 41.28 | 42.33 |
| 31 | 38.54 | 39.15 |
| 32 | 48.84 | 46.19 |
| 33 | 61.56 | 54.98 |
| 34 | 52.68 | 48.79 |
| 35 | 47.69 | 45.15 |
| 36 | 34.69 | 39.49 |
| 37 | 57.45 | 56.32 |

-continued

| Patient | Serum HDL | Normalized HDL |
|---|---|---|
| 38 | 38.00 | 36.33 |
| 39 | 47.53 | 42.14 |
| 40 | 60.04 | 58.94 |
| 41 | 36.08 | 37.35 |
| 42 | 46.09 | 48.37 |
| 43 | 42.22 | 42.82 |
| 44 | 34.70 | 38.98 |
| 45 | 55.76 | 55.79 |
| 46 | 21.16 | 24.53 |
| 47 | 55.33 | 55.69 |
| 48 | 44.66 | 42.65 |
| 49 | 83.26 | 81.00 |
| 50 | 44.33 | 46.14 |
| 51 | 40.71 | 40.69 |
| 52 | 47.24 | 43.98 |
| 53 | 49.46 | 47.71 |
| 54 | 44.37 | 43.30 |
| 55 | 50.16 | 48.34 |
| 56 | 55.49 | 61.30 |
| 57 | 49.27 | 45.94 |
| 58 | 51.73 | 51.78 |
| 59 | 38.07 | 36.98 |
| 60 | 38.22 | 38.49 |
| 61 | 43.57 | 45.05 |
| 62 | 54.16 | 51.46 |
| 63 | 38.66 | 34.13 |
| 64 | 50.14 | 48.65 |
| 65 | 57.94 | 54.11 |
| 66 | 46.02 | 44.67 |
| 67 | 49.21 | 52.36 |
| 68 | 43.15 | 45.31 |
| 69 | 37.20 | 38.42 |
| 70 | 49.66 | 50.00 |
| 71 | 63.00 | 65.28 |
| 72 | 79.92 | 79.17 |
| 73 | 37.12 | 44.57 |
| 74 | 59.14 | 60.35 |
| 75 | 32.49 | 28.57 |
| 76 | 56.08 | 59.37 |
| 77 | 64.22 | 70.04 |
| 78 | 46.54 | 48.66 |
| 79 | 37.68 | 37.28 |
| 80 | 75.41 | 74.70 |
| 81 | 44.06 | 44.73 |
| 82 | 40.65 | 40.88 |
| 83 | 93.40 | 91.97 |
| 84 | 40.97 | 47.04 |
| 85 | 69.63 | 75.17 |
| 86 | 36.13 | 38.81 |
| 87 | 34.88 | 36.42 |
| 88 | 43.90 | 49.40 |
| 89 | 63.29 | 66.41 |
| 90 | 49.21 | 49.65 |
| 91 | 29.54 | 31.27 |
| 92 | 49.30 | 49.87 |
| 93 | 35.82 | 34.39 |
| 94 | 49.66 | 51.20 |
| 95 | 39.01 | 39.79 |
| 96 | 36.92 | 34.49 |
| 97 | 43.40 | 43.45 |
| 98 | 48.70 | 45.97 |
| 99 | 42.15 | 41.04 |
| 100 | 59.09 | 55.11 |
| 101 | 49.46 | 47.04 |
| 102 | 33.36 | 29.81 |
| 103 | 49.36 | 47.93 |
| 104 | 43.02 | 39.12 |
| 105 | 39.81 | 41.06 |
| 106 | 60.29 | 56.62 |
| 107 | 59.84 | 55.33 |
| 108 | 84.77 | 82.31 |
| 109 | 55.20 | 55.72 |
| 110 | 54.77 | 56.06 |
| 111 | 69.16 | 67.30 |
| 112 | 38.18 | 40.50 |
| 113 | 37.11 | 36.49 |
| 114 | 51.31 | 49.24 |

-continued

| Patient | Serum HDL | Normalized HDL |
|---|---|---|
| 115 | 39.69 | 42.54 |
| 116 | 61.17 | 56.56 |
| 117 | 29.94 | 30.25 |
| 118 | 75.50 | 77.62 |
| 119 | 56.94 | 57.49 |
| 120 | 68.89 | 71.30 |
| 121 | 37.89 | 40.82 |
| 122 | 73.57 | 72.14 |
| 123 | 78.31 | 78.16 |
| 124 | 48.88 | 47.45 |
| 125 | 83.96 | 79.26 |
| 126 | 95.12 | 92.48 |
| 127 | 51.44 | 52.50 |
| 128 | 38.88 | 38.10 |
| 129 | 41.70 | 44.58 |
| 130 | 47.80 | 46.24 |
| 131 | 56.42 | 59.35 |
| 132 | 55.14 | 56.98 |

A comparative linear regression was generated for the data points collected in this Example. The linear fit followed the following equation:

$$\text{Normalized HDL} = 2.47 + 0.953 \times \text{Serum HDL},$$

with the correlation coefficient, expressed as $R^2$, being greater than 0.96.

EXAMPLE 7

This example demonstrates the performance of the invention in the measurement of triglycerides (TG). The dried spots and venous blood specimens from the same one hundred thirty-two patients in Example 5 were used to measure TG in capillary blood and compare it to a measured value for TG in venous blood. The normalized TG evel in capillary blood was obtained according to the present invention using the formula: Normalized TG=Measured TG/(A+B×(Measured Sodium/139)), where A and B were obtained as previously described. The following results were observed.

| Patient | Serum TG | Normalized TG |
|---|---|---|
| 1 | 73.24 | 55.65 |
| 2 | 97.89 | 97.31 |
| 3 | 45.26 | 38.38 |
| 4 | 70.31 | 60.30 |
| 5 | 119.71 | 119.33 |
| 6 | 105.97 | 100.56 |
| 7 | 77.47 | 73.30 |
| 8 | 220.18 | 236.94 |
| 9 | 191.79 | 203.18 |
| 10 | 177.10 | 177.03 |
| 11 | 112.19 | 116.71 |
| 12 | 73.24 | 55.65 |
| 13 | 97.89 | 97.31 |
| 14 | 45.26 | 38.38 |
| 15 | 70.31 | 60.30 |
| 16 | 119.71 | 119.33 |
| 17 | 157.70 | 164.69 |
| 18 | 122.09 | 124.56 |
| 19 | 66.86 | 63.24 |
| 20 | 138.31 | 151.08 |
| 21 | 146.08 | 137.36 |
| 22 | 95.85 | 97.05 |
| 23 | 77.27 | 60.69 |
| 24 | 85.44 | 82.87 |
| 25 | 86.25 | 77.32 |
| 26 | 112.51 | 110.68 |

-continued

| Patient | Serum TG | Normalized TG |
|---|---|---|
| 27 | 176.25 | 184.16 |
| 28 | 190.63 | 189.57 |
| 29 | 95.17 | 98.92 |
| 30 | 98.52 | 98.76 |
| 31 | 102.13 | 97.07 |
| 32 | 117.77 | 128.91 |
| 33 | 123.08 | 125.56 |
| 34 | 135.72 | 132.69 |
| 35 | 76.46 | 71.14 |
| 36 | 230.90 | 210.77 |
| 37 | 80.41 | 67.66 |
| 38 | 99.43 | 85.63 |
| 39 | 86.87 | 91.07 |
| 40 | 125.01 | 120.98 |
| 41 | 362.90 | 322.04 |
| 42 | 132.98 | 118.47 |
| 43 | 83.21 | 75.43 |
| 44 | 52.45 | 53.34 |
| 45 | 53.91 | 50.52 |
| 46 | 349.76 | 357.87 |
| 47 | 135.25 | 139.57 |
| 48 | 209.20 | 208.33 |
| 49 | 374.36 | 386.86 |
| 50 | 74.90 | 79.81 |
| 51 | 395.31 | 399.34 |
| 52 | 56.38 | 54.87 |
| 53 | 217.08 | 258.78 |
| 54 | 52.83 | 71.35 |
| 55 | 136.53 | 144.81 |
| 56 | 115.98 | 118.45 |
| 57 | 78.41 | 62.45 |
| 58 | 70.38 | 65.13 |
| 59 | 91.00 | 68.59 |
| 60 | 180.98 | 179.72 |
| 61 | 163.32 | 188.88 |
| 62 | 72.16 | 65.05 |
| 63 | 102.89 | 101.45 |
| 64 | 50.24 | 49.05 |
| 65 | 184.45 | 195.42 |
| 66 | 183.07 | 194.25 |
| 67 | 65.28 | 65.04 |
| 68 | 111.40 | 109.43 |
| 69 | 67.25 | 87.27 |
| 70 | 74.92 | 72.25 |
| 71 | 100.19 | 105.33 |
| 72 | 136.82 | 132.52 |
| 73 | 119.29 | 129.90 |
| 74 | 119.76 | 119.83 |
| 75 | 121.90 | 125.90 |
| 76 | 75.55 | 80.65 |
| 77 | 74.44 | 89.06 |
| 78 | 226.78 | 243.05 |
| 79 | 71.19 | 78.23 |
| 80 | 98.89 | 93.66 |
| 81 | 127.93 | 135.56 |
| 82 | 333.65 | 352.31 |
| 83 | 97.18 | 91.96 |
| 84 | 139.77 | 133.20 |
| 85 | 73.23 | 72.05 |
| 86 | 160.00 | 148.64 |
| 87 | 131.69 | 133.49 |
| 88 | 69.07 | 66.79 |
| 89 | 271.22 | 248.43 |
| 90 | 91.86 | 98.00 |
| 91 | 231.14 | 224.76 |
| 92 | 153.65 | 171.85 |
| 93 | 115.95 | 107.16 |
| 94 | 263.50 | 257.68 |
| 95 | 95.38 | 92.85 |
| 96 | 143.96 | 125.21 |
| 97 | 110.10 | 131.36 |
| 98 | 97.72 | 93.75 |
| 99 | 158.22 | 151.23 |
| 100 | 123.80 | 127.26 |
| 101 | 279.56 | 271.61 |
| 102 | 192.26 | 176.02 |
| 103 | 59.41 | 59.23 |
| 104 | 197.04 | 186.32 |
| 105 | 182.29 | 170.98 |
| 106 | 96.16 | 91.53 |
| 107 | 80.46 | 72.56 |
| 108 | 65.55 | 68.16 |
| 109 | 215.37 | 210.92 |
| 110 | 186.09 | 191.14 |
| 111 | 96.41 | 96.52 |
| 112 | 78.68 | 80.54 |
| 113 | 83.96 | 73.13 |
| 114 | 207.32 | 208.03 |
| 115 | 37.41 | 37.32 |
| 116 | 103.17 | 93.38 |
| 117 | 193.21 | 210.21 |
| 118 | 119.46 | 103.27 |
| 119 | 67.57 | 58.99 |
| 120 | 119.56 | 117.34 |
| 121 | 75.42 | 52.90 |
| 122 | 311.18 | 315.01 |
| 123 | 67.72 | 68.28 |
| 124 | 127.36 | 129.28 |
| 125 | 59.82 | 64.57 |
| 126 | 85.54 | 83.90 |
| 127 | 43.24 | 41.49 |
| 128 | 85.09 | 78.05 |
| 129 | 95.15 | 99.45 |
| 130 | 92.21 | 75.05 |
| 131 | 72.46 | 88.51 |
| 132 | 56.52 | 57.13 |

A comparative linear regression was generated for the data points collected in this Example. The linear fit followed the following equation:

Normalized $TG = -2.5 + 1.01 \times$ Serum $TG$, with the coefficient, expressed as $R^2$, being 0.98.

EXAMPLE 8

This example demonstrates the performance of the invention in the measurement of LDL. The same observations from the same one hundred thirty-two patients in Example 5, 6 and 7 were used to calculate a value for LDL in serum and a value for LDL in MSS according to the Friedewald formula:

Serum LDL=Serum Cholesterol−Serum HDL−Serum $TG/5$

Normalized LDL=Normalized Cholesterol−Normalized HDL−Normalized $TG/5$.

The following results were calculated:

| Patient | Serum LDL | Normalized LDL |
|---|---|---|
| 1 | 110.85 | 101.31 |
| 2 | 97.93 | 101.60 |
| 3 | 109.82 | 103.89 |
| 4 | 110.51 | 112.89 |
| 5 | 108.21 | 107.74 |
| 6 | 126.07 | 121.49 |
| 7 | 49.76 | 54.13 |
| 8 | 173.19 | 173.53 |
| 9 | 78.72 | 77.71 |
| 10 | 129.52 | 119.61 |
| 11 | 174.74 | 180.58 |
| 12 | 149.04 | 140.09 |
| 13 | 98.72 | 101.13 |
| 14 | 115.22 | 115.25 |
| 15 | 187.28 | 180.56 |

-continued

| Patient | Serum LDL | Normalized LDL |
|---|---|---|
| 16 | 146.29 | 158.21 |
| 17 | 195.20 | 200.00 |
| 18 | 167.30 | 161.22 |
| 19 | 101.87 | 99.92 |
| 20 | 122.26 | 127.45 |
| 21 | 168.27 | 164.79 |
| 22 | 149.27 | 148.28 |
| 23 | 100.92 | 85.06 |
| 24 | 129.40 | 115.93 |
| 25 | 92.09 | 88.71 |
| 26 | 165.02 | 175.92 |
| 27 | 114.88 | 104.61 |
| 28 | 94.16 | 90.62 |
| 29 | 154.94 | 142.87 |
| 30 | 114.95 | 117.39 |
| 31 | 144.71 | 148.13 |
| 32 | 152.62 | 164.12 |
| 33 | 105.78 | 111.48 |
| 34 | 105.62 | 106.95 |
| 35 | 101.99 | 102.99 |
| 36 | 143.96 | 145.31 |
| 37 | 119.65 | 105.96 |
| 38 | 68.65 | 63.55 |
| 39 | 78.02 | 75.16 |
| 40 | 180.50 | 174.23 |
| 41 | 110.10 | 109.10 |
| 42 | 72.00 | 80.58 |
| 43 | 124.52 | 118.94 |
| 44 | 140.68 | 128.72 |
| 45 | 165.02 | 178.66 |
| 46 | 92.96 | 83.43 |
| 47 | 145.15 | 156.72 |
| 48 | 133.07 | 131.63 |
| 49 | 105.59 | 101.08 |
| 50 | 177.71 | 184.34 |
| 51 | 102.56 | 101.25 |
| 52 | 91.72 | 95.09 |
| 53 | 123.82 | 129.64 |
| 54 | 194.21 | 203.38 |
| 55 | 144.23 | 138.11 |
| 56 | 120.42 | 125.06 |
| 57 | 120.22 | 122.32 |
| 58 | 87.42 | 84.13 |
| 59 | 107.19 | 106.80 |
| 60 | 130.18 | 120.03 |
| 61 | 124.30 | 115.07 |
| 62 | 151.99 | 156.98 |
| 63 | 61.89 | 58.86 |
| 64 | 111.54 | 110.38 |
| 65 | 128.43 | 143.14 |
| 66 | 150.60 | 143.35 |
| 67 | 150.93 | 153.10 |
| 68 | 84.28 | 81.94 |
| 69 | 68.95 | 66.01 |
| 70 | 101.92 | 98.27 |
| 71 | 104.27 | 101.79 |
| 72 | 106.22 | 98.91 |
| 73 | 93.38 | 96.56 |
| 74 | 72.72 | 73.88 |
| 75 | 63.90 | 56.58 |
| 76 | 111.92 | 111.11 |
| 77 | 160.96 | 155.60 |
| 78 | 118.95 | 118.43 |
| 79 | 80.19 | 77.42 |
| 80 | 92.68 | 91.67 |
| 81 | 99.78 | 95.56 |
| 82 | 82.00 | 84.09 |
| 83 | 105.58 | 108.07 |
| 84 | 133.61 | 128.66 |
| 85 | 130.44 | 134.49 |
| 86 | 87.08 | 90.07 |
| 87 | 85.82 | 87.16 |
| 88 | 150.87 | 147.80 |
| 89 | 123.40 | 126.22 |
| 90 | 80.33 | 84.64 |
| 91 | 78.47 | 76.28 |
| 92 | 107.81 | 97.16 |
| 93 | 65.74 | 66.47 |
| 94 | 84.06 | 81.90 |
| 95 | 53.88 | 67.10 |
| 96 | 97.42 | 95.63 |
| 97 | 119.93 | 127.83 |
| 98 | 72.69 | 79.87 |
| 99 | 144.28 | 143.36 |
| 100 | 149.12 | 140.94 |
| 101 | 96.03 | 102.76 |
| 102 | 101.29 | 102.50 |
| 103 | 101.09 | 108.85 |
| 104 | 109.96 | 117.58 |
| 105 | 136.29 | 126.72 |
| 106 | 107.05 | 107.20 |
| 107 | 87.89 | 91.28 |
| 108 | 143.01 | 153.30 |
| 109 | 135.15 | 134.00 |
| 110 | 109.68 | 108.74 |
| 111 | 117.33 | 123.38 |
| 112 | 128.59 | 126.45 |
| 113 | 96.53 | 98.88 |
| 114 | 126.58 | 129.56 |
| 115 | 128.60 | 131.36 |
| 116 | 117.26 | 116.58 |
| 117 | 165.65 | 155.24 |
| 118 | 89.27 | 80.15 |
| 119 | 121.23 | 125.97 |
| 120 | 129.51 | 146.03 |
| 121 | 152.74 | 162.44 |
| 122 | 117.83 | 124.94 |
| 123 | 121.01 | 125.32 |
| 124 | 122.19 | 111.80 |
| 125 | 190.94 | 178.21 |
| 126 | 118.95 | 115.83 |
| 127 | 108.85 | 110.95 |
| 128 | 76.17 | 84.41 |
| 129 | 116.38 | 120.15 |
| 130 | 116.39 | 113.82 |
| 131 | 134.85 | 142.75 |
| 132 | 173.09 | 172.40 |

A comparative linear regression was generated for the data points collected in this Example. The linear fit followed the following equation:

Normalized LDL=−0.25+1.00×Serum LDL, with the correlation, expressed as $R^2$, being equal to 0.96.

EXAMPLE 9

This example demonstrates the measurement of total cholesterol.

Sixty-six patients were used to obtain blood via venal puncture (venous blood specimens) and by pricking their fingers (capillary blood specimens). Capillary blood was spotted on xylose-coated Whatman GF/AVA filter paper, using a device similar to that shown in FIG. 9. Capillary blood specimens were dried and the portion of the filter paper that contained separated serum was cut out and eluted in 8 batches. Eluate from each specimen was measured for cholesterol, sodium and chloride on Cobas Mira (Roche, Indianapolis, Ind.). The normalized cholesterol level was obtained according to the present invention using a formula: Normalized Cholesterol=(Na-Normalized Cholesterol+Cl-Normalized Cholesterol)/2, where Na-Normalized Cholesterol was equal to (Measured Cholesterol−Cholesterol RD)/(0.0070311+0.8157416×(Fixed Slope Sodium−Sodium Background)/Population Mean Na)) and Cl-Normalized Cholesterol was equal to (Measured Cholesterol−Cholesterol RD)/(−0.04833+0.7458044×(Fixed Slope Chloride−Chloride Background)/Population Mean CL)). In this equation, A1, B1 and A2, B2 were scalar values that were recalculated based on the "tare" procedure heretofore described, whereby a regression for six patients was calculated and the intercept and slope values from this regression were used to calculate normalized cholesterol values for specimens. Cholesterol RD was equal to 0.10 mg/dL. Fixed Slope Sodium was equal to Measured Sodium (or Na)×10 exponent [Log 10 (Na/150)× (Na Slope−Na Fixed Slope)/Na Fixed Slope], where Na Fixed Slope=55.7. Fixed Slope Chloride was equal to Measured Chloride (or Cl)×10 exponent [Log 10 (Cl/138)×(Cl Slope−Cl Fixed Slope)/Cl Fixed Slope], where Cl Fixed Slope=55.28. Sodium and Chloride background was equal to 13.32 mEq/L and 12.2 mEq/L. Actual (directly measured in venous blood) and calculated normalized cholesterol values for these patients are given below.

| Sample | Measured CHO | Na-Norm CHO | Cl-Norm CHO | MSS_CHO | Serum CHO | Measured NA | Measured CL | Bg-Na | Bg-CL | Na Slope | Cl Slope |
|---|---|---|---|---|---|---|---|---|---|---|---|
| 201 | 208 | 253 | 249 | 251 | 268 | 154 | 135 | 13.32 | 12.20 | 57.37 | −39.18 |
| 205 | 231 | 172 | 170 | 171 | 175 | 241 | 249 | 13.32 | 12.20 | 57.37 | −39.18 |
| 206 | 155 | 189 | 188 | 188 | 191 | 153 | 134 | 13.32 | 12.20 | 57.37 | −39.18 |
| 207 | 311 | 277 | 272 | 275 | 288 | 204 | 201 | 13.32 | 12.20 | 57.37 | −39.18 |
| 208 | 164 | 164 | 163 | 163 | 167 | 184 | 171 | 13.32 | 12.20 | 57.37 | −39.18 |
| 210 | 145 | 266 | 258 | 262 | 256 | 108 | 85 | 13.32 | 12.20 | 57.37 | −39.18 |
| 211 | 190 | 271 | 271 | 271 | 258 | 133 | 110 | 13.32 | 12.20 | 57.37 | −39.18 |
| 212 | 108 | 201 | 200 | 201 | 185 | 106 | 81 | 13.32 | 12.20 | 57.37 | −39.18 |
| 213 | 188 | 195 | 199 | 197 | 206 | 178 | 158 | 13.32 | 12.20 | 57.37 | −39.18 |
| 214 | 134 | 139 | 138 | 138 | 153 | 179 | 163 | 13.32 | 12.20 | 57.37 | −39.18 |
| 215 | 218 | 206 | 209 | 208 | 198 | 193 | 179 | 13.32 | 12.20 | 57.37 | −39.18 |
| 216 | 130 | 247 | 244 | 245 | 254 | 105 | 81 | 13.32 | 12.20 | 60.07 | −40.37 |
| 217 | 221 | 215 | 216 | 216 | 214 | 187 | 173 | 13.32 | 12.20 | 60.07 | −40.37 |
| 219 | 138 | 203 | 204 | 203 | 221 | 131 | 106 | 13.32 | 12.20 | 60.07 | −40.37 |
| 220 | 228 | 199 | 197 | 198 | 211 | 205 | 202 | 13.32 | 12.20 | 60.07 | −40.37 |
| 223 | 138 | 195 | 194 | 194 | 193 | 136 | 113 | 13.32 | 12.20 | 60.07 | −40.37 |
| 227 | 283 | 243 | 246 | 245 | 261 | 208 | 199 | 13.32 | 12.20 | 60.07 | −40.37 |
| 230 | 79 | 154 | 157 | 156 | 143 | 103 | 74 | 13.32 | 12.20 | 58.56 | −38.21 |
| 233 | 89 | 174 | 189 | 182 | 170 | 103 | 69 | 13.32 | 12.20 | 58.56 | −38.21 |
| 234 | 135 | 202 | 210 | 206 | 196 | 129 | 99 | 13.32 | 12.20 | 58.56 | −38.21 |
| 236 | 103 | 135 | 139 | 137 | 134 | 144 | 118 | 13.32 | 12.20 | 58.56 | −38.21 |
| 237 | 115 | 192 | 199 | 195 | 200 | 118 | 88 | 13.32 | 12.20 | 58.56 | −38.21 |
| 238 | 154 | 192 | 199 | 196 | 204 | 151 | 124 | 13.32 | 12.20 | 58.56 | −38.21 |
| 239 | 77 | 111 | 114 | 112 | 117 | 132 | 104 | 13.32 | 12.20 | 58.56 | −38.21 |
| 240 | 95 | 155 | 143 | 149 | 165 | 119 | 102 | 13.32 | 12.20 | 58.12 | −38.21 |
| 241 | 115 | 178 | 183 | 180 | 197 | 124 | 96 | 13.32 | 12.20 | 58.12 | −38.21 |
| 242 | 104 | 190 | 195 | 193 | 211 | 108 | 79 | 13.32 | 12.20 | 58.12 | −38.21 |
| 243 | 107 | 209 | 211 | 210 | 227 | 102 | 75 | 13.32 | 12.20 | 58.12 | −38.21 |
| 244 | 104 | 185 | 189 | 187 | 194 | 110 | 82 | 13.32 | 12.20 | 58.12 | −38.21 |
| 245 | 153 | 176 | 174 | 175 | 178 | 162 | 144 | 13.32 | 12.20 | 58.12 | −38.21 |
| 246 | 248 | 312 | 320 | 316 | 314 | 150 | 124 | 13.32 | 12.20 | 58.12 | −38.21 |
| 247 | 137 | 229 | 230 | 230 | 233 | 117 | 90 | 13.32 | 12.20 | 58.12 | −38.21 |
| 248 | 109 | 207 | 209 | 208 | 210 | 104 | 77 | 13.32 | 12.20 | 58.12 | −38.21 |
| 250 | 80 | 138 | 139 | 138 | 144 | 113 | 86 | 13.32 | 12.20 | 58.12 | −38.21 |
| 254 | 184 | 193 | 193 | 193 | 192 | 176 | 161 | 13.32 | 12.20 | 58.12 | −38.21 |
| 255 | 145 | 168 | 163 | 166 | 167 | 161 | 147 | 13.32 | 12.20 | 57.69 | −38.32 |
| 256 | 108 | 168 | 159 | 164 | 172 | 124 | 105 | 13.32 | 12.20 | 57.69 | −38.32 |
| 257 | 101 | 192 | 192 | 192 | 188 | 104 | 78 | 13.32 | 12.20 | 57.69 | −38.32 |
| 258 | 223 | 305 | 308 | 307 | 308 | 138 | 114 | 13.32 | 12.20 | 57.69 | −38.32 |
| 261 | 310 | 300 | 296 | 298 | 291 | 189 | 181 | 13.32 | 12.20 | 57.69 | −38.32 |
| 262 | 228 | 171 | 169 | 170 | 172 | 239 | 251 | 13.32 | 12.20 | 57.69 | −38.32 |
| 263 | 214 | 190 | 190 | 190 | 192 | 204 | 197 | 13.32 | 12.20 | 57.69 | −38.32 |
| 264 | 256 | 238 | 237 | 237 | 240 | 196 | 188 | 13.32 | 12.20 | 57.69 | −38.32 |
| 265 | 232 | 205 | 205 | 205 | 201 | 205 | 199 | 13.32 | 12.20 | 57.69 | −38.32 |
| 266 | 328 | 296 | 293 | 295 | 302 | 201 | 196 | 13.32 | 12.20 | 57.69 | −38.32 |
| 267 | 177 | 208 | 205 | 207 | 198 | 159 | 141 | 13.32 | 12.20 | 58.02 | −42.32 |
| 270 | 137 | 188 | 182 | 185 | 191 | 138 | 120 | 13.32 | 12.20 | 58.02 | −42.32 |
| 271 | 356 | 285 | 275 | 280 | 289 | 225 | 226 | 13.32 | 12.20 | 58.02 | −42.32 |
| 274 | 178 | 185 | 184 | 185 | 193 | 177 | 161 | 13.32 | 12.20 | 58.02 | −42.32 |
| 275 | 267 | 226 | 226 | 226 | 233 | 213 | 202 | 13.32 | 12.20 | 58.02 | −42.32 |
| 276 | 235 | 210 | 214 | 212 | 207 | 203 | 187 | 13.32 | 12.20 | 58.02 | −42.32 |
| 277 | 286 | 227 | 226 | 227 | 229 | 225 | 220 | 13.32 | 12.20 | 58.02 | −42.32 |
| 278 | 154 | 170 | 169 | 169 | 172 | 168 | 149 | 13.32 | 12.20 | 58.02 | −42.32 |
| 279 | 194 | 153 | 146 | 149 | 151 | 227 | 233 | 13.32 | 12.20 | 58.02 | −42.32 |
| 280 | 155 | 302 | 303 | 302 | 282 | 102 | 80 | 13.32 | 12.20 | 58.02 | −42.32 |
| 283 | 99 | 184 | 178 | 181 | 189 | 106 | 87 | 13.32 | 12.20 | 58.02 | −42.32 |
| 284 | 144 | 192 | 183 | 188 | 188 | 142 | 127 | 13.32 | 12.20 | 58.02 | −42.32 |
| 301 | 101 | 173 | 170 | 171 | 179 | 114 | 95 | 13.32 | 12.20 | 57.04 | −43.30 |
| 302 | 124 | 180 | 178 | 179 | 170 | 131 | 112 | 13.32 | 12.20 | 57.04 | −43.30 |
| 305 | 197 | 220 | 217 | 219 | 229 | 166 | 150 | 13.32 | 12.20 | 57.04 | −43.30 |
| 306 | 124 | 191 | 190 | 191 | 198 | 125 | 104 | 13.32 | 12.20 | 57.04 | −43.30 |
| 307 | 227 | 247 | 250 | 249 | 235 | 171 | 150 | 13.32 | 12.20 | 57.04 | −43.30 |
| 308 | 220 | 239 | 236 | 238 | 243 | 170 | 153 | 13.32 | 12.20 | 57.04 | −43.30 |
| 310 | 151 | 235 | 235 | 235 | 237 | 124 | 102 | 13.32 | 12.20 | 57.04 | −43.30 |

-continued

| Sample | Measured CHO | Na-Norm CHO | Cl-Norm CHO | MSS_CHO | Serum CHO | Measured NA | Measured CL | Bg-Na | Bg-CL | Na Slope | Cl Slope |
|---|---|---|---|---|---|---|---|---|---|---|---|
| 311 | 136 | 247 | 241 | 244 | 234 | 108 | 90 | 13.32 | 12.20 | 57.04 | −43.30 |
| 313 | 169 | 234 | 236 | 235 | 240 | 137 | 115 | 13.32 | 12.20 | 57.04 | −43.30 |

A comparative linear regression was generated for the data points collected in this Example. The linear fit followed the following equation:

Normalized Cholesterol (MSS CHO)=−1.7+0.996× Serum Cholesterol, with the correlation coefficient, expressed as $R^2$, being 0. 0.960.

EXAMPLE 10

This example demonstrates the performance of the invention in the measurement of HDL. The dried spots and venous blood specimens from the same sixty-six patients in Example 9 were used to measure HDL in capillary blood and compare it to a value for HDL in venous blood. The normalized HDL level in capillary blood was obtained according to the present invention using the following formula: Normalized HDL= (Na-Normalized HDL+Cl-Normalized HDL)/2, where Na-Normalized HDL was equal to (Measured HDL−HDL RD)/ (0.0326271+0.8120791×(Fixed Slope Sodium−Sodium Background)/Population Mean Na)) and Cl-Normalized HDL was equal to (Measured HDL−HDL RD)/(−0.021347+ 0.7416995×(Fixed Slope Chloride−Chloride Background)/ Population Mean CL)), where intercept A and slope B were obtained as previously described. HDL RD was calculated as 0.0342×Measured Cholesterol and Sodium and Chloride Background was the same as in the Example 9. The following results were observed.

| Sample | Measured HDL | Na-Norm HDL | Cl-Norm HDL | MSS_HDL | Serum HDL | Measured NA | Measured CL | HDL-RD | Bg-Na | Bg-CL | Na Slope | Cl Slope |
|---|---|---|---|---|---|---|---|---|---|---|---|---|
| 201 | 54 | 55 | 55 | 55 | 58 | 154 | 135 | 7.10 | 13.32 | 12.20 | 57.37 | −39.18 |
| 205 | 81 | 54 | 53 | 53 | 54 | 241 | 249 | 7.90 | 13.32 | 12.20 | 57.37 | −39.18 |
| 206 | 39 | 40 | 40 | 40 | 40 | 153 | 134 | 5.29 | 13.32 | 12.20 | 57.37 | −39.18 |
| 207 | 50 | 35 | 34 | 35 | 37 | 204 | 201 | 10.65 | 13.32 | 12.20 | 57.37 | −39.18 |
| 208 | 68 | 61 | 61 | 61 | 62 | 184 | 171 | 5.60 | 13.32 | 12.20 | 57.37 | −39.18 |
| 210 | 62 | 100 | 97 | 99 | 91 | 108 | 85 | 4.97 | 13.32 | 12.20 | 57.37 | −39.18 |
| 211 | 42 | 50 | 50 | 50 | 48 | 133 | 110 | 6.49 | 13.32 | 12.20 | 57.37 | −39.18 |
| 212 | 41 | 67 | 67 | 67 | 60 | 106 | 81 | 3.70 | 13.32 | 12.20 | 57.37 | −39.18 |
| 213 | 55 | 49 | 50 | 50 | 48 | 178 | 158 | 6.45 | 13.32 | 12.20 | 57.37 | −39.18 |
| 214 | 57 | 53 | 53 | 53 | 58 | 179 | 163 | 4.59 | 13.32 | 12.20 | 57.37 | −39.18 |
| 215 | 81 | 69 | 69 | 69 | 65 | 193 | 179 | 7.46 | 13.32 | 12.20 | 57.37 | −39.18 |
| 216 | 32 | 51 | 50 | 51 | 55 | 105 | 81 | 4.43 | 13.32 | 12.20 | 60.07 | −40.37 |
| 217 | 69 | 59 | 59 | 59 | 57 | 187 | 173 | 7.55 | 13.32 | 12.20 | 60.07 | −40.37 |
| 219 | 35 | 44 | 44 | 44 | 47 | 131 | 106 | 4.71 | 13.32 | 12.20 | 60.07 | −40.37 |
| 220 | 65 | 49 | 48 | 49 | 49 | 205 | 202 | 7.79 | 13.32 | 12.20 | 60.07 | −40.37 |
| 223 | 35 | 42 | 42 | 42 | 41 | 136 | 113 | 4.72 | 13.32 | 12.20 | 60.07 | −40.37 |
| 227 | 73 | 53 | 54 | 54 | 50 | 208 | 199 | 9.67 | 13.32 | 12.20 | 60.07 | −40.37 |
| 230 | 33 | 56 | 57 | 57 | 53 | 103 | 74 | 2.71 | 13.32 | 12.20 | 58.56 | −38.21 |
| 233 | 27 | 45 | 48 | 46 | 45 | 103 | 69 | 3.05 | 13.32 | 12.20 | 58.56 | −38.21 |
| 234 | 81 | 111 | 115 | 113 | 108 | 129 | 99 | 4.63 | 13.32 | 12.20 | 58.56 | −38.21 |
| 236 | 39 | 45 | 46 | 45 | 40 | 144 | 118 | 3.53 | 13.32 | 12.20 | 58.56 | −38.21 |
| 237 | 44 | 65 | 67 | 66 | 66 | 118 | 88 | 3.95 | 13.32 | 12.20 | 58.56 | −38.21 |
| 238 | 36 | 37 | 39 | 38 | 39 | 151 | 124 | 5.28 | 13.32 | 12.20 | 58.56 | −38.21 |
| 239 | 29 | 38 | 39 | 38 | 37 | 132 | 104 | 2.62 | 13.32 | 12.20 | 58.56 | −38.21 |
| 240 | 31 | 44 | 41 | 43 | 44 | 119 | 102 | 3.24 | 13.32 | 12.20 | 58.12 | −38.21 |
| 241 | 35 | 46 | 47 | 47 | 47 | 124 | 96 | 3.92 | 13.32 | 12.20 | 58.12 | −38.21 |
| 242 | 34 | 54 | 55 | 55 | 58 | 108 | 79 | 3.55 | 13.32 | 12.20 | 58.12 | −38.21 |
| 243 | 21 | 32 | 32 | 32 | 30 | 102 | 75 | 3.67 | 13.32 | 12.20 | 58.12 | −38.21 |
| 244 | 22 | 32 | 33 | 32 | 36 | 110 | 82 | 3.54 | 13.32 | 12.20 | 58.12 | −38.21 |
| 245 | 58 | 59 | 59 | 59 | 57 | 162 | 144 | 5.22 | 13.32 | 12.20 | 58.12 | −38.21 |
| 246 | 76 | 83 | 85 | 84 | 83 | 150 | 124 | 8.49 | 13.32 | 12.20 | 58.12 | −38.21 |
| 247 | 32 | 44 | 45 | 45 | 47 | 117 | 90 | 4.70 | 13.32 | 12.20 | 58.12 | −38.21 |
| 248 | 24 | 36 | 36 | 36 | 34 | 104 | 77 | 3.71 | 13.32 | 12.20 | 58.12 | −38.21 |
| 250 | 35 | 53 | 53 | 53 | 61 | 113 | 86 | 2.73 | 13.32 | 12.20 | 58.12 | −38.21 |
| 254 | 56 | 51 | 51 | 51 | 46 | 176 | 161 | 6.30 | 13.32 | 12.20 | 58.12 | −38.21 |
| 255 | 59 | 61 | 59 | 60 | 56 | 161 | 147 | 4.98 | 13.32 | 12.20 | 57.69 | −38.32 |
| 256 | 55 | 77 | 73 | 75 | 70 | 124 | 105 | 3.68 | 13.32 | 12.20 | 57.69 | −38.32 |
| 257 | 54 | 92 | 92 | 92 | 91 | 104 | 78 | 3.46 | 13.32 | 12.20 | 57.69 | −38.32 |
| 258 | 35 | 37 | 37 | 37 | 40 | 138 | 114 | 7.62 | 13.32 | 12.20 | 57.69 | −38.32 |
| 261 | 93 | 79 | 78 | 78 | 79 | 189 | 181 | 10.61 | 13.32 | 12.20 | 57.69 | −38.32 |
| 262 | 79 | 53 | 52 | 52 | 53 | 239 | 251 | 7.80 | 13.32 | 12.20 | 57.69 | −38.32 |
| 263 | 68 | 53 | 53 | 53 | 55 | 204 | 197 | 7.31 | 13.32 | 12.20 | 57.69 | −38.32 |
| 264 | 91 | 75 | 75 | 75 | 75 | 196 | 188 | 8.75 | 13.32 | 12.20 | 57.69 | −38.32 |
| 265 | 90 | 71 | 71 | 71 | 69 | 205 | 199 | 7.93 | 13.32 | 12.20 | 57.69 | −38.32 |

-continued

| Sample | Measured HDL | Na-Norm HDL | Cl-Norm HDL | MSS_HDL | Serum HDL | Measured NA | Measured CL | HDL-RD | Bg-Na | Bg-CL | Na Slope | Cl Slope |
|---|---|---|---|---|---|---|---|---|---|---|---|---|
| 266 | 64 | 47 | 46 | 46 | 43 | 201 | 196 | 11.21 | 13.32 | 12.20 | 57.69 | −38.32 |
| 267 | 51 | 51 | 51 | 51 | 46 | 159 | 141 | 6.07 | 13.32 | 12.20 | 58.02 | −42.32 |
| 270 | 39 | 46 | 44 | 45 | 41 | 138 | 120 | 4.67 | 13.32 | 12.20 | 58.02 | −42.32 |
| 271 | 89 | 61 | 59 | 60 | 60 | 225 | 226 | 12.18 | 13.32 | 12.20 | 58.02 | −42.32 |
| 274 | 45 | 40 | 40 | 40 | 40 | 177 | 161 | 6.10 | 13.32 | 12.20 | 58.02 | −42.32 |
| 275 | 82 | 61 | 61 | 61 | 61 | 213 | 202 | 9.14 | 13.32 | 12.20 | 58.02 | −42.32 |
| 276 | 59 | 44 | 45 | 45 | 42 | 203 | 187 | 8.05 | 13.32 | 12.20 | 58.02 | −42.32 |
| 277 | 49 | 30 | 30 | 30 | 31 | 225 | 220 | 9.77 | 13.32 | 12.20 | 58.02 | −42.32 |
| 278 | 50 | 48 | 48 | 48 | 49 | 168 | 149 | 5.26 | 13.32 | 12.20 | 58.02 | −42.32 |
| 279 | 63 | 44 | 42 | 43 | 43 | 227 | 233 | 6.62 | 13.32 | 12.20 | 58.02 | −42.32 |
| 280 | 39 | 63 | 63 | 63 | 54 | 102 | 80 | 5.31 | 13.32 | 12.20 | 58.02 | −42.32 |
| 283 | 25 | 39 | 38 | 39 | 42 | 106 | 87 | 3.38 | 13.32 | 12.20 | 58.02 | −42.32 |
| 284 | 51 | 59 | 57 | 58 | 57 | 142 | 127 | 4.91 | 13.32 | 12.20 | 58.02 | −42.32 |
| 301 | 29 | 43 | 42 | 42 | 45 | 114 | 95 | 3.46 | 13.32 | 12.20 | 57.04 | −43.30 |
| 302 | 41 | 52 | 51 | 52 | 51 | 131 | 112 | 4.23 | 13.32 | 12.20 | 57.04 | −43.30 |
| 305 | 47 | 44 | 43 | 43 | 48 | 166 | 150 | 6.75 | 13.32 | 12.20 | 57.04 | −43.30 |
| 306 | 32 | 41 | 41 | 41 | 37 | 125 | 104 | 4.25 | 13.32 | 12.20 | 57.04 | −43.30 |
| 307 | 51 | 46 | 47 | 47 | 44 | 171 | 150 | 7.78 | 13.32 | 12.20 | 57.04 | −43.30 |
| 308 | 72 | 68 | 68 | 68 | 69 | 170 | 153 | 7.52 | 13.32 | 12.20 | 57.04 | −43.30 |
| 310 | 37 | 48 | 48 | 48 | 45 | 124 | 102 | 5.17 | 13.32 | 12.20 | 57.04 | −43.30 |
| 311 | 22 | 30 | 29 | 30 | 30 | 108 | 90 | 4.67 | 13.32 | 12.20 | 57.04 | −43.30 |
| 313 | 53 | 64 | 64 | 64 | 63 | 137 | 115 | 5.77 | 13.32 | 12.20 | 57.04 | −43.30 |

A comparative linear regression was generated for the data points collected in this Example. The linear fit followed the following equation:

Normalized HDL=−1.2+1.035×Serum HDL, with the correlation coefficient, expressed as $R^2$, being greater than 0.961.

EXAMPLE 11

This example demonstrates the performance of the invention in the measurement of triglycerides. The dried spots and venous blood specimens from the same sixty-six patients in Example 9 were used to measure triglycerides in capillary blood and compare it to a value for triglycerides in venous blood. The normalized triglycerides level in capillary blood was obtained according to the present invention using a formula: Normalized Triglycerides=(Na-Normalized Triglycerides+Cl-Normalized Triglycerides)/2, where Na-Normalized Triglycerides was equal to (Measured Triglycerides−Triglycerides RD)/(0.0814243+0.5536861×(Fixed Slope Sodium−Sodium Background)/Population Mean Na)) and Cl-Normalized Triglycerides was equal to (Measured Triglycerides−Triglycerides RD)/(0.0419903+0.5074508×(Fixed Slope Chloride−Chloride Background)/Population Mean CL)). Normalized Triglycerides=(Measured Triglycerides−Triglycerides RD)/(A+B×(Measured Sodium/139)), where A and B were obtained as previously described. Triglycerides RD was equal to −4.51 mg/dL and Sodium and Chloride Background was the same as in the Example 9.

The following results were observed.

| Sample | Measured TG | Na-Norm CHO | Na-Norm TG | Cl-Norm TG | MSS_TG | Serum TG | Measured NA | Measured CL | TG RD | Bg-Na | Bg-CL | Na Slope | Cl Slope |
|---|---|---|---|---|---|---|---|---|---|---|---|---|---|
| 201 | 45 | 253 | 78 | 77 | 78 | 83 | 154 | 135 | −4.51 | 13.32 | 13.32 | 57.37 | −39.18 |
| 205 | 79 | 172 | 84 | 83 | 84 | 93 | 241 | 249 | −4.51 | 13.32 | 12.20 | 57.37 | −39.18 |
| 206 | 42 | 189 | 74 | 73 | 73 | 78 | 153 | 134 | −4.51 | 13.32 | 12.20 | 57.37 | −39.18 |
| 207 | 160 | 277 | 196 | 193 | 195 | 208 | 204 | 201 | −4.51 | 13.32 | 12.20 | 57.37 | −39.18 |
| 208 | 21 | 164 | 34 | 34 | 34 | 35 | 184 | 171 | −4.51 | 13.32 | 12.20 | 57.37 | −39.18 |
| 210 | 23 | 266 | 62 | 60 | 61 | 66 | 108 | 85 | −4.51 | 13.32 | 12.20 | 57.37 | −39.18 |
| 211 | 107 | 271 | 202 | 202 | 202 | 196 | 133 | 110 | −4.51 | 13.32 | 12.20 | 57.37 | −39.18 |
| 212 | 90 | 201 | 215 | 215 | 215 | 197 | 106 | 81 | −4.51 | 13.32 | 12.20 | 57.37 | −39.18 |
| 213 | 156 | 195 | 219 | 223 | 221 | 198 | 178 | 158 | −4.51 | 13.32 | 12.20 | 57.37 | −39.18 |
| 214 | 69 | 139 | 100 | 100 | 100 | 85 | 179 | 163 | −4.51 | 13.32 | 12.20 | 57.37 | −39.18 |
| 215 | 67 | 206 | 90 | 91 | 90 | 88 | 193 | 179 | −4.51 | 13.32 | 12.20 | 57.37 | −39.18 |
| 216 | 103 | 247 | 250 | 247 | 248 | 201 | 105 | 81 | −4.51 | 13.32 | 12.20 | 60.07 | −40.37 |
| 217 | 91 | 215 | 123 | 124 | 124 | 105 | 187 | 173 | −4.51 | 13.32 | 12.20 | 60.07 | −40.37 |
| 219 | 102 | 203 | 199 | 200 | 200 | 156 | 131 | 106 | −4.51 | 13.32 | 12.20 | 60.07 | −40.37 |
| 220 | 75 | 199 | 93 | 92 | 92 | 82 | 205 | 202 | −4.51 | 13.32 | 12.20 | 60.07 | −40.37 |
| 223 | 73 | 195 | 140 | 139 | 139 | 133 | 136 | 113 | −4.51 | 13.32 | 12.20 | 60.07 | −40.37 |
| 227 | 184 | 243 | 217 | 220 | 218 | 205 | 208 | 199 | −4.51 | 13.32 | 12.20 | 60.07 | −40.37 |
| 230 | 20 | 154 | 57 | 58 | 57 | 51 | 103 | 74 | −4.51 | 13.32 | 12.20 | 58.56 | −38.21 |
| 233 | 38 | 174 | 101 | 109 | 105 | 96 | 103 | 69 | −4.51 | 13.32 | 12.20 | 58.56 | −38.21 |
| 234 | 49 | 202 | 101 | 104 | 102 | 84 | 129 | 99 | −4.51 | 13.32 | 12.20 | 58.56 | −38.21 |
| 236 | 73 | 135 | 130 | 133 | 132 | 118 | 144 | 118 | −4.51 | 13.32 | 12.20 | 58.56 | −38.21 |

-continued

| Sample | Measured TG | Na-Norm CHO | Na-Norm TG | Cl-Norm TG | MSS_TG | Serum TG | Measured NA | Measured CL | TG RD | Bg-Na | Bg-CL | Na Slope | Cl Slope |
|---|---|---|---|---|---|---|---|---|---|---|---|---|---|
| 237 | 28 | 192 | 67 | 69 | 68 | 58 | 118 | 88 | −4.51 | 13.32 | 12.20 | 58.56 | −38.21 |
| 238 | 42 | 192 | 76 | 78 | 77 | 82 | 151 | 124 | −4.51 | 13.32 | 12.20 | 58.56 | −38.21 |
| 239 | 35 | 111 | 72 | 74 | 73 | 57 | 132 | 104 | −4.51 | 13.32 | 12.20 | 58.56 | −38.21 |
| 240 | 50 | 155 | 112 | 105 | 108 | 98 | 119 | 102 | −4.51 | 13.32 | 12.20 | 58.12 | −38.21 |
| 241 | 20 | 178 | 47 | 48 | 48 | 56 | 124 | 96 | −4.51 | 13.32 | 12.20 | 58.12 | −38.21 |
| 242 | 57 | 190 | 138 | 142 | 140 | 144 | 108 | 79 | −4.51 | 13.32 | 12.20 | 58.12 | −38.21 |
| 243 | 101 | 209 | 248 | 250 | 249 | 268 | 102 | 75 | −4.51 | 13.32 | 12.20 | 58.12 | −38.21 |
| 244 | 153 | 185 | 345 | 351 | 348 | 424 | 110 | 82 | −4.51 | 13.32 | 12.20 | 58.12 | −38.21 |
| 245 | 45 | 176 | 74 | 74 | 74 | 66 | 162 | 144 | −4.51 | 13.32 | 12.20 | 58.12 | −38.21 |
| 246 | 39 | 312 | 71 | 73 | 72 | 77 | 150 | 124 | −4.51 | 13.32 | 12.20 | 58.12 | −38.21 |
| 247 | 39 | 229 | 90 | 91 | 91 | 93 | 117 | 90 | −4.51 | 13.32 | 12.20 | 58.12 | −38.21 |
| 248 | 49 | 207 | 124 | 125 | 124 | 132 | 104 | 77 | −4.51 | 13.32 | 12.20 | 58.12 | −38.21 |
| 250 | 23 | 138 | 58 | 59 | 58 | 47 | 113 | 86 | −4.51 | 13.32 | 12.20 | 58.12 | −38.21 |
| 254 | 59 | 193 | 87 | 87 | 87 | 84 | 176 | 161 | −4.51 | 13.32 | 12.20 | 58.12 | −38.21 |
| 255 | 132 | 168 | 205 | 200 | 203 | 190 | 161 | 147 | −4.51 | 13.32 | 12.20 | 57.69 | −38.32 |
| 256 | 23 | 168 | 53 | 51 | 52 | 47 | 124 | 105 | −4.51 | 13.32 | 12.20 | 57.69 | −38.32 |
| 257 | 25 | 192 | 68 | 68 | 68 | 66 | 104 | 78 | −4.51 | 13.32 | 12.20 | 57.69 | −38.32 |
| 258 | 89 | 305 | 164 | 165 | 164 | 165 | 138 | 114 | −4.51 | 13.32 | 12.20 | 57.69 | −38.32 |
| 261 | 80 | 300 | 108 | 107 | 107 | 107 | 189 | 181 | −4.51 | 13.32 | 12.20 | 57.69 | −38.32 |
| 262 | 48 | 171 | 53 | 53 | 53 | 59 | 239 | 251 | −4.51 | 13.32 | 12.20 | 57.69 | −38.32 |
| 263 | 71 | 190 | 90 | 91 | 91 | 93 | 204 | 197 | −4.51 | 13.32 | 12.20 | 57.69 | −38.32 |
| 264 | 45 | 238 | 61 | 61 | 61 | 69 | 196 | 188 | −4.51 | 13.32 | 12.20 | 57.69 | −38.32 |
| 265 | 40 | 205 | 53 | 53 | 53 | 55 | 205 | 199 | −4.51 | 13.32 | 12.20 | 57.69 | −38.32 |
| 266 | 395 | 296 | 482 | 478 | 480 | 501 | 201 | 196 | −4.51 | 13.32 | 12.20 | 57.69 | −38.32 |
| 267 | 133 | 208 | 211 | 208 | 209 | 205 | 159 | 141 | −4.51 | 13.32 | 12.20 | 58.02 | −42.32 |
| 270 | 121 | 188 | 221 | 215 | 218 | 217 | 138 | 120 | −4.51 | 13.32 | 12.20 | 58.02 | −42.32 |
| 271 | 111 | 285 | 124 | 121 | 122 | 127 | 225 | 226 | −4.51 | 13.32 | 12.20 | 58.02 | −42.32 |
| 274 | 75 | 185 | 108 | 108 | 108 | 115 | 177 | 161 | −4.51 | 13.32 | 12.20 | 58.02 | −42.32 |
| 275 | 83 | 226 | 99 | 99 | 99 | 109 | 213 | 202 | −4.51 | 13.32 | 12.20 | 58.02 | −42.32 |
| 276 | 177 | 210 | 217 | 220 | 218 | 208 | 203 | 187 | −4.51 | 13.32 | 12.20 | 58.02 | −42.32 |
| 277 | 300 | 227 | 328 | 325 | 326 | 309 | 225 | 220 | −4.51 | 13.32 | 12.20 | 58.02 | −42.32 |
| 278 | 43 | 170 | 69 | 69 | 69 | 73 | 168 | 149 | −4.51 | 13.32 | 12.20 | 58.02 | −42.32 |
| 279 | 60 | 153 | 68 | 66 | 67 | 76 | 227 | 233 | −4.51 | 13.32 | 12.20 | 58.02 | −42.32 |
| 280 | 74 | 302 | 186 | 186 | 186 | 184 | 102 | 80 | −4.51 | 13.32 | 12.20 | 58.02 | −42.32 |
| 283 | 24 | 184 | 65 | 63 | 64 | 68 | 106 | 87 | −4.51 | 13.32 | 12.20 | 58.02 | −42.32 |
| 284 | 62 | 192 | 115 | 110 | 112 | 106 | 142 | 127 | −4.51 | 13.32 | 12.20 | 58.02 | −42.32 |
| 301 | 32 | 173 | 78 | 77 | 77 | 75 | 114 | 95 | −4.51 | 13.32 | 12.20 | 57.04 | −43.30 |
| 302 | 59 | 180 | 116 | 115 | 116 | 95 | 131 | 112 | −4.51 | 13.32 | 12.20 | 57.04 | −43.30 |
| 305 | 92 | 220 | 142 | 140 | 141 | 158 | 166 | 150 | −4.51 | 13.32 | 12.20 | 57.04 | −43.30 |
| 306 | 35 | 191 | 77 | 77 | 77 | 84 | 125 | 104 | −4.51 | 13.32 | 12.20 | 57.04 | −43.30 |
| 307 | 144 | 247 | 211 | 214 | 212 | 201 | 171 | 150 | −4.51 | 13.32 | 12.20 | 57.04 | −43.30 |
| 308 | 71 | 239 | 109 | 107 | 108 | 111 | 170 | 153 | −4.51 | 13.32 | 12.20 | 57.04 | −43.30 |
| 310 | 84 | 235 | 172 | 172 | 172 | 174 | 124 | 102 | −4.51 | 13.32 | 12.20 | 57.04 | −43.30 |
| 311 | 438 | 247 | 982 | 962 | 972 | 989 | 108 | 90 | −4.51 | 13.32 | 12.20 | 57.04 | −43.30 |
| 313 | 43 | 234 | 84 | 85 | 85 | 87 | 137 | 115 | −4.51 | 13.32 | 12.20 | 57.04 | −43.30 |

A comparative linear regression was generated for the data points collected in this Example. The linear fit followed the following equation:

Normalized $TG = 6.4 + 0.967 \times \text{Serum } TG$, with the coefficient, expressed as $R^2$, being 0.987.

EXAMPLE 12

This example demonstrates the performance of the invention in the measurement of LDL. The same observations from the same six patients in Example 9, 10 and 11 were used to calculate a value for LDL in serum and a value for LDL in MSS according to the Friedewald formula:

Serum LDL = Serum Cholesterol − Serum HDL − Serum $TG/5$

Normalized LDL = Normalized Cholesterol − Normalized HDL − Normalized $TG/5$.

LDL was not calculated when Triglycerides were above 400 mg/dL.

The following results were calculated:

| Sample | MSS_CHO | MSS_HDL | MSS_TG | MSS_LDL | Serum LDL |
|---|---|---|---|---|---|
| 201 | 251 | 55 | 78 | 181 | 194 |
| 205 | 171 | 53 | 84 | 101 | 102 |
| 206 | 188 | 40 | 73 | 134 | 136 |
| 207 | 275 | 35 | 195 | 201 | 210 |
| 208 | 163 | 61 | 34 | 95 | 98 |
| 210 | 262 | 99 | 61 | 151 | 152 |
| 211 | 271 | 50 | 202 | 181 | 171 |
| 212 | 201 | 67 | 215 | 91 | 86 |
| 213 | 197 | 50 | 221 | 103 | 118 |
| 214 | 138 | 53 | 100 | 65 | 78 |
| 215 | 208 | 69 | 90 | 121 | 115 |
| 216 | 245 | 51 | 248 | 145 | 159 |
| 217 | 216 | 59 | 124 | 132 | 137 |
| 219 | 203 | 44 | 200 | 120 | 142 |
| 220 | 198 | 49 | 92 | 131 | 146 |
| 223 | 194 | 42 | 139 | 125 | 125 |
| 227 | 245 | 54 | 218 | 147 | 170 |
| 230 | 156 | 57 | 57 | 88 | 80 |
| 233 | 182 | 46 | 105 | 114 | 106 |

-continued

| Sample | MSS_CHO | MSS_HDL | MSS_TG | MSS_LDL | Serum LDL |
|---|---|---|---|---|---|
| 234 | 206 | 113 | 102 | 73 | 71 |
| 236 | 137 | 45 | 132 | 65 | 70 |
| 237 | 195 | 66 | 68 | 116 | 123 |
| 238 | 196 | 38 | 77 | 142 | 149 |
| 239 | 112 | 38 | 73 | 59 | 68 |
| 240 | 149 | 43 | 108 | 85 | 101 |
| 241 | 180 | 47 | 48 | 124 | 139 |
| 242 | 193 | 55 | 140 | 110 | 124 |
| 243 | 210 | 32 | 249 | 128 | 143 |
| 244 | 187 | 32 | 348 | 85 | 74 |
| 245 | 175 | 59 | 74 | 101 | 108 |
| 246 | 316 | 84 | 72 | 218 | 216 |
| 247 | 230 | 45 | 91 | 167 | 167 |
| 248 | 208 | 36 | 124 | 147 | 150 |
| 250 | 138 | 53 | 58 | 73 | 74 |
| 254 | 193 | 51 | 87 | 124 | 129 |
| 255 | 166 | 60 | 203 | 65 | 73 |
| 256 | 164 | 75 | 52 | 78 | 92 |
| 257 | 192 | 92 | 68 | 86 | 84 |
| 258 | 307 | 37 | 164 | 237 | 235 |
| 261 | 298 | 78 | 107 | 199 | 191 |
| 262 | 170 | 52 | 53 | 107 | 107 |
| 263 | 190 | 53 | 91 | 119 | 119 |
| 264 | 237 | 75 | 61 | 150 | 152 |
| 265 | 205 | 71 | 53 | 124 | 120 |
| 266 | 295 | 46 | 480 | | |
| 267 | 207 | 51 | 209 | 114 | 110 |
| 270 | 185 | 45 | 218 | 97 | 106 |
| 271 | 280 | 60 | 122 | 196 | 203 |
| 274 | 185 | 40 | 108 | 123 | 129 |
| 275 | 226 | 61 | 99 | 146 | 150 |
| 276 | 212 | 45 | 218 | 123 | 123 |
| 277 | 227 | 30 | 326 | 131 | 136 |
| 278 | 169 | 48 | 69 | 107 | 108 |
| 279 | 149 | 43 | 67 | 93 | 93 |
| 280 | 302 | 63 | 186 | 202 | 192 |
| 283 | 181 | 39 | 64 | 130 | 134 |
| 284 | 188 | 58 | 112 | 107 | 109 |
| 301 | 171 | 42 | 77 | 113 | 119 |
| 302 | 179 | 52 | 116 | 104 | 100 |
| 305 | 219 | 43 | 141 | 147 | 150 |
| 306 | 191 | 41 | 77 | 134 | 144 |
| 307 | 249 | 47 | 212 | 159 | 151 |
| 308 | 238 | 68 | 108 | 148 | 151 |
| 310 | 235 | 48 | 172 | 153 | 157 |
| 311 | 244 | 30 | 972 | | |
| 313 | 235 | 64 | 85 | 154 | 160 |

A comparative linear regression was generated for the data points collected in this Example. The linear fit followed the following equation:

Normalized LDL=−2.49+0.99×Serum LDL, with the correlation, expressed. as $R^2$, being equal to 0.960.

It is thus seen that the invention provides a method for determining the level of an analyte in a specimen.

While particular embodiments to the invention have been described herein, the invention is not limited thereto, but to the contrary should be deemed defined by the full scope of the appended claims. All references and prior and co-pending applications cited herein are hereby incorporated by reference in their entireties.

What is claimed is:

1. A method for determining the level of an analyte in blood from a solution formed from a dried blood fluid specimen, said blood fluid specimen being a plasma or serum specimen, comprising: in either order, measuring the analyte level in said solution and measuring the level of at least one normalizing analyte; and determining the analyte level in the blood from which said blood fluid specimen was collected based on said analyte level in said solution and on the level of said normalizing analyte in said solution, wherein, in determining the analyte level in the blood from which said blood fluid specimen was collected, a recovery delta is added to the analyte level of the analyte level in said solution to provide a recovery delta corrected solution analyte level, and the analyte level in the blood from which said blood fluid specimen was collected is determined as a function of said recovery delta corrected solution analyte level and on the level of said normalizing analyte, wherein said recovery delta is a positive value, wherein said recovery delta is determined as a function of the time elapsed since said blood fluid specimen was collected.

2. A method according to claim 1, wherein said recovery delta is determined in accordance with the function: A+B (time) wherein A is 0, a positive value, or a negative value, and B is a positive or negative non-zero value.

3. A method according to claim 2, wherein B is determined based on climactic conditions.

4. A method according to claim 1, said analyte being selected from the group consisting of total cholesterol, HDL, LDL, and TG.

5. A method according to claim 1, said normalizing analyte including sodium.

6. A method according to claim 1, said normalizing analyte including chloride.

7. A method for determining the level of an analyte in blood from a solution formed from a dried blood fluid specimen, said blood fluid specimen being a plasma or serum specimen, comprising: in either order, measuring the analyte level in said solution and measuring the level of at least one normalizing analyte; and determining the analyte level in the blood from which said blood fluid specimen was collected based on said analyte level in said solution and on the level of said normalizing analyte in said solution, wherein, in determining the analyte level in the blood from which said blood fluid specimen was collected, a recovery delta is added to the analyte level of the analyte level in said solution to provide a recovery delta corrected solution analyte level, and the analyte level in the blood from which said blood fluid specimen was collected is determined as a function of said recovery delta corrected solution analyte level and on the level of said normalizing analyte, wherein said recovery delta is a negative value, wherein said recovery delta is determined as a function of the time elapsed since said blood fluid specimen was collected.

8. A method for determining the level of an analyte in blood from a solution formed from a dried blood fluid specimen, said blood fluid specimen being a plasma or serum specimen, comprising: in either order, measuring the analyte level in said solution and measuring the level of at least a first normalizing analyte; and determining an analyte level in the blood from which said blood fluid specimen was collected based on said analyte level in said solution and on the level of said first normalizing analyte in said solution, wherein the calculation of analyte level in the blood from which said blood fluid specimen was taken includes a predetermined nonlinear first analyte correction factor, measuring the level of at least a second normalizing analyte in said solution, wherein the level of analyte in the blood from which said blood fluid specimen was collected is determined based on the level of said second normalizing analyte and on the corrected first analyte level.

9. A method according to claim 8, wherein a first blood analyte level is determined based on the levels in solution of said analyte and said chloride normalizing analyte; a second blood analyte level is determined based on the levels in solution of said analyte and said second normalizing analyte; and the level of analyte in the blood from which said blood fluid specimen was collected is determined by calculating the mean average of said first and second blood analyte levels.

10. A method according to claim 9, said first normalizing analyte comprising chloride.

11. A method for reporting a test result, comprising:
receiving an incoming inquiry from a user;
prompting said user for a test number;
retrieving a test result from a database of test numbers and test results; and
reporting said test result to said user, said test result comprising an analyte level having been determined according to a method for determining the level of an analyte in blood from a solution formed from a dried blood fluid specimen, said blood fluid specimen being a plasma or serum specimen, comprising: in either order, measuring the analyte level in said solution and measuring the level of at least one normalizing analyte; and determining the analyte level in the blood from which said blood fluid specimen was collected based on said analyte level in said solution and on the level of said normalizing analyte in said solution, wherein, in determining the analyte level in the blood from which said blood fluid specimen was collected, a recovery delta is added to the analyte level of the analyte level in said solution to provide a recovery delta corrected solution analyte level, and the analyte level in the blood from which said blood fluid specimen was collected is determined as a function of said recovery delta corrected solution analyte level and on the level of said normalizing analyte.

12. A method for reporting a test result, comprising:
receiving an incoming inquiry from a user;
prompting said user for a test number;
retrieving a test result from a database of test numbers and test results; and
reporting said test result to said user, said test result comprising an analyte level having been determined according to a method for determining the level of an analyte in blood from a solution formed from a dried blood fluid specimen, said blood fluid specimen being a plasma or serum specimen, comprising: in either order, measuring the analyte level in said solution and measuring the level of at least a first normalizing analyte; and determining the analyte level in the blood from which said blood fluid specimen was collected based on said analyte level in said solution and on the level of said first normalizing analyte in said solution, wherein the calculation of analyte level in the blood from which said blood fluid specimen was taken includes a predetermined nonlinear first analyte correction factor.

* * * * *